(12) United States Patent
Lewis et al.

(10) Patent No.: US 11,468,784 B2
(45) Date of Patent: Oct. 11, 2022

(54) DIGITAL PHYSIOLOGICAL NEUROCOGNITIVE AND BEHAVIORAL IMPAIRMENT ASSESSMENT SYSTEMS AND METHODS OF USING THE SAME

(71) Applicant: Driveability VT, LLC, South Burlington, VT (US)

(72) Inventors: Christopher Lewis, South Burlington, VT (US); Andy Kaplan, Burlington, VT (US); Ari Kirshenbaum, Lincoln, VT (US); Gershon Parent, Port Orchard, WA (US); Jevan Fox, Venice, CA (US)

(73) Assignee: Driveability VT, LLC, South Burlington, VT (US)

( * ) Notice: Subject to any disclaimer, the term of this patent is extended or adjusted under 35 U.S.C. 154(b) by 69 days.

(21) Appl. No.: 16/948,379

(22) Filed: Sep. 16, 2020

(65) Prior Publication Data

US 2021/0082306 A1 Mar. 18, 2021

Related U.S. Application Data

(60) Provisional application No. 62/900,712, filed on Sep. 16, 2019.

(51) Int. Cl.
*G09B 19/00* (2006.01)
*G16H 50/20* (2018.01)
(Continued)

(52) U.S. Cl.
CPC .......... *G09B 19/00* (2013.01); *G06F 16/245* (2019.01); *G16H 10/60* (2018.01); *G16H 20/10* (2018.01); *G16H 50/20* (2018.01)

(58) Field of Classification Search
CPC ............. G16H 10/60; G16H 50/20–30; G16H 20/10–30; G16H 70/40; G06F 16/245;
(Continued)

(56) References Cited

U.S. PATENT DOCUMENTS 6,280,198 B1 8/2001 Calhoun et al.
8,308,562 B2 11/2012 Patton
(Continued)

FOREIGN PATENT DOCUMENTS

WO 2020152678 A1 7/2020

OTHER PUBLICATIONS

J. Orlosky, Y. Itoh, M. Ranchet, K. Kiyokawa, J. Morgan and H. Devos, "Emulation of Physician Tasks in Eye-Tracked Virtual Reality for Remote Diagnosis of Neurodegenerative Disease," in IEEE Transactions on Visualization and Computer Graphics, vol. 23, No. 4, pp. 1302-1311, Apr. 2017. (Year: 2017).*
(Continued)

*Primary Examiner* — Robert J Utama
*Assistant Examiner* — Correll T French
(74) *Attorney, Agent, or Firm* — Downs Rachlin Martin PLLC

(57) ABSTRACT

Interactive software applications designed to assess a combination of behavioral neuro-physiological characteristics of a user to determine an effect a substance is currently having on the user. In some examples the effect of the substance may be assessed to identify a cognitive impairment caused by a substance and determine the type of substance(s) likely causing the impairment. In some examples the effect of the substance may be assessed to determine a recommended dosage and/or a standard impairing dose threshold for a particular substance.

27 Claims, 27 Drawing Sheets

(51) Int. Cl.
 *G06F 16/245* (2019.01)
 *G16H 10/60* (2018.01)
 *G16H 20/10* (2018.01)
(58) Field of Classification Search
 CPC . A61B 5/1104; A61B 5/16; A61B 5/162–165;
  G09B 9/00; G09B 19/00; A63F 13/00;
  A63F 13/20; A63F 13/537; A63F 13/69
 See application file for complete search history.

(56) References Cited

U.S. PATENT DOCUMENTS

| | | | |
|---|---|---|---|
| 8,899,748 | B1 | 12/2014 | Migdal |
| 9,302,179 | B1* | 4/2016 | Merzenich ............... G09B 5/00 |
| 10,004,431 | B2 | 6/2018 | Shuster et al. |
| 10,040,458 | B2 | 8/2018 | Morley et al. |
| 10,390,802 | B1 | 8/2019 | Picard et al. |
| 11,129,524 | B2* | 9/2021 | Ally ......................... A61B 3/02 |
| 2008/0146892 | A1* | 6/2008 | LeBoeuf ............... A61B 5/6803 600/300 |
| 2009/0082640 | A1 | 3/2009 | Kovach .................... A61B 5/24 600/300 |
| 2014/0107429 | A1* | 4/2014 | Simkovich ........... A61B 5/4088 600/300 |
| 2015/0051508 | A1 | 2/2015 | Ghajar et al. |
| 2016/0073945 | A1* | 3/2016 | Fine ....................... G16Z 99/00 600/558 |
| 2017/0049362 | A1* | 2/2017 | Macknik ............... A61B 5/4845 |
| 2017/0367633 | A1 | 12/2017 | Samadani |
| 2018/0140250 | A1 | 5/2018 | Sweetman |
| 2019/0150819 | A1 | 5/2019 | Charvat et al. |
| 2019/0298245 | A1* | 10/2019 | Jarmolkowicz ...... A61B 5/4076 |
| 2020/0029880 | A1 | 1/2020 | Katnani et al. |
| 2020/0121235 | A1* | 4/2020 | Gibbons ............... A61B 5/0077 |
| 2020/0405215 | A1* | 12/2020 | Tinjust ................. A61B 5/7405 |

OTHER PUBLICATIONS

Suffoletto, et al., "Can an App Help Identify Psychomotor Function Impairments During Drinking Occasions in the Real World? A Mixed Method Pilot Study ." https://www.ncbi.nlm.nih.gov/pmc/articles/PMC6103191/. Aug. 21, 2018, pp. 1-17.

Mariakakis et al., "Drunk User Interfaces: Determining Blood Alcohol Level through Everyday Smartphone Tasks." CHI 2018, Apr. 21-26, 2018, pp. 1-13.

Richman, et al., "An Investigation of the Druid® Smartphone/Tablet App as a Rapid Screening Assessment for Cognitive and Psychomotor Impairment Associated With Alcohol Intoxication." Vision Development & Rehabilitation, vol. 5, Issue 1, Mar. 2019, pp. 31-42.

L'Heureux, "There's An App for That: Technology to Check Your Level of Impairment." https://www.cannabissciencetech.com/view/theres-app-technology-check-your-level-impairment. May 1, 2019.

Innocorp Inc. "7 Drunk Goggles Activities For Your Alcohol Awareness Program." https://www.fatalvision.com/blog/drunk-goggles-alcohol-awareness-activities/, Oct. 3, 2019.

Intarasirisawat, et al., "An Automated Mobile Game-based Screening Tool for Patients with Alcohol Dependence." Proc. ACM Interact. Mob. Wearable Ubiquitous Technology, vol. 1, No. 1, Jul. 2020.

Benedek et al., "Creativity on tap? Effects of alcohol intoxication on creative cognition." Consciousness and Cognition, Jul. 10, 2017, pp. 128-134.

Corazzini et al., "Economic Behavior under the Influence of Alcohol: An Experiment on Time Preferences, Risk-Taking, and Altruism." https://journals.plos.org/plosone/article?id=10.1371/journal.pone.0121530, Apr. 8, 2015.

"New App could make cannabis use safer." https://www.eurekalert.org/pub_releases/2018-04/eb2-nac041318.php , Experimental Biology, Apr. 24, 2018.

Gonzalez, "Too High, Drunk, or Sleepy to Drive? One Day Your Phone Could Know." https://www.wired.com/story/portable-field-sobriety-tests/, Science Apr. 30, 2018.

Myers, "Smartphone app tests user's level of alcohol impairment"; https://www.ems1.com/ems-products/technology/articles/smartphone-app-tests-users-level-of-alcohol-impairment-g51QKVhH1pZiiqHU/; Dec. 14, 2014.

* cited by examiner

DIGITAL PHYSIOLOGICAL NEUROCOGNITIVE AND BEHAVIORAL IMPAIRMENT ASSESSMENT SYSTEMS AND METHODS OF USING THE SAME

RELATED APPLICATION DATA

This application claims the benefit of priority of U.S. Provisional Patent Application Ser. No. 62/900,712, filed Sep. 16, 2019, and titled "Digital Impairment Assessment Apparatus and Method", which is incorporated by reference herein in its entirety.

FIELD OF THE DISCLOSURE

The present disclosure generally relates to the field of physiological neurocognitive and behavioral impairment assessment. In particular, the present disclosure is directed to digital physiological neurocognitive behavioral impairment assessment systems and methods of using the same.

BACKGROUND

Evidence of increased traffic fatalities in states with a legalized cannabis retail-market is mounting. The problem of impaired driving will continue to grow into the foreseeable future due to the ever-increasing public acceptance of cannabis-related products and a legislative landscape that is responsive to constituents. Impaired motor vehicle operation accidents, including automobiles and other motorized equipment, costs the nation hundreds of billions of dollars per year, with insurers and employers ultimately paying a majority of those costs. Law enforcement and employers currently have no tool to detect the presence of cognitive and behavioral impairment from cannabinoids. While biological-sampling methods in development, such as saliva and blood tests may be able to detect a history of cannabinoid use, they do not accurately portray the recency of use nor the degree to which a driver's cognitive aptitudes required for the safe operation of the vehicle may be impaired.

Determining a proper dosage of a substance such as marijuana can also be challenging. Substance dispensaries and prescribers such as marijuana dispensaries and medical providers may want to determine a recommended potency and dosage for a particular product type and delivery method, e.g., flower, oil, edible, vapor, etc. Similarly, consumers may want to determine a proper personalized dosage for a particular type of marijuana, for example, to achieve a desired effect over time.

SUMMARY OF THE DISCLOSURE

In one implementation, the present disclosure is directed to a method of performing an impairment assessment with an impairment assessment application executed on a computing device. The method includes selecting and executing, by a processor, a plurality of cognitive tests, each of the cognitive tests in the form of a video game displayed on a user interface of the computing device, wherein the video games include at least one of: a first video game configured to test psychomotor compensation and including instructions for execution by a processor for displaying a user control element and an object on the user interface, the object configured to move in a periodic or random manner, the user control element for controlling a position of the object in response to the periodic or random movements of the object; a second video game configured to test a user's sense of timing and including instructions for execution by a processor for displaying at least one time-varying stimuli, the second video game configured to test a user's ability to recall and predict a time duration of the time varying stimuli; and a third video game configured to test a user's sustained attention and divided attention and including instructions for execution by a processor for displaying sequences of symbols for the user to remember and recognize; processing, by the processor, user performance data from the user's performance of the cognitive tests; and determining, by the processor, an impairment assessment from the user performance data.

In another implementation, the present disclosure is directed to a method of performing a physiological neurocognitive and/or behavioral assessment with an impairment assessment system, the system including a cloud-based impairment assessment service and a user device. The method includes executing a first video game on the user device, the executing the first video game including: displaying on a user interface of the user device, a user control element and an object; moving the object in a plurality of directions on the user interface; receiving user controls via the user control element to control a position of the object in response to the moving of the object; collecting user performance data on the user's ability to control the position of the object; calculating a user performance variable for psychomotor control according to the user performance data from the first video game; executing a second video game on the user device, the executing the second video game including: displaying at least one example time-varying stimuli on the user interface of the user device; receiving user control signals via the user interface representing when the user predicts the time-varying stimuli will be displayed according to the example time-varying stimuli; collecting user performance data on the user's ability to predict when the time-varying stimuli would be displayed; calculating a user performance variable for a sense of timing according to the user performance data from the second video game; and executing a third video game on the user device, the executing the third video game including: displaying a time-varying sequence of symbols that include a target sequence; receiving user control signals via the user interface representing when the user observes the target sequence; collecting user performance data on the user's ability to observe when the target sequence is displayed; calculating a user performance variable for sustained attention and short term memory according to the user performance data from the third video game.

In yet another implementation, the present disclosure is directed to a method of performing a physiological neurocognitive and/or behavioral assessment with an impairment assessment system, the system including a cloud-based impairment assessment service, and a user device, the impairment assessment service including a plurality of plurality of video games configured to test cognitive aptitudes, and a database of user performance data, the method includes presenting a first one of the plurality of video games on the user device; receiving, at the impairment assessment service, user performance data from the user's performance on the first video game; selecting, by the impairment assessment service, a second one of the plurality of video games according to the user performance data from the user's performance on the first video game; presenting the second one of the plurality of video games on the user device; receiving, at the impairment assessment service, user performance data from the user's performance on the second video game; determining an impairment assessment according to the user performance data from the user's performance on the first and second video games.

BRIEF DESCRIPTION OF THE DRAWINGS

For the purpose of illustrating the disclosure, the drawings show aspects of one or more embodiments of the disclosure. However, it should be understood that the present disclosure is not limited to the precise arrangements and instrumentalities shown in the drawings, wherein:

FIG. 4 shows example cognitive aptitudes that cognitive tests of the present disclosure may be designed to test for;

FIGS. 16A-16M are example questionnaires that a questionnaire module may be configured to display on a user interface to collect questionnaire data;

DETAILED DESCRIPTION

Aspects of the present disclosure include systems and methods designed to present interactive software applications to a user on an electronic device, the applications designed to assess a combination of behavioral neurophysiological characteristics of the user to determine an effect a substance is currently having on the user. The effect of the substance may be assessed for a variety of purposes, such as the presence or absence of cognitive impairment, the impairment of cognitive aptitudes useful for operating a motor vehicle or equipment or performing related tasks requiring specific aptitudes. In some examples, whether the degree of impairment globally, and/or for specific cognitive aptitudes is above a threshold value, such as a legal limit, or a limit associated with intoxication. In some examples the effect of the substance may be assessed to identify cognitive impairment caused by a substance and determine the type of substance(s) likely causing the impairment. In some examples the effect of the substance may be assessed to determine a recommended dosage and/or a standard impairing dose threshold for a particular substance. In some examples the effect of the substance may be assessed to determine a user's personalized dosage for a particular substance.

Figure 1:
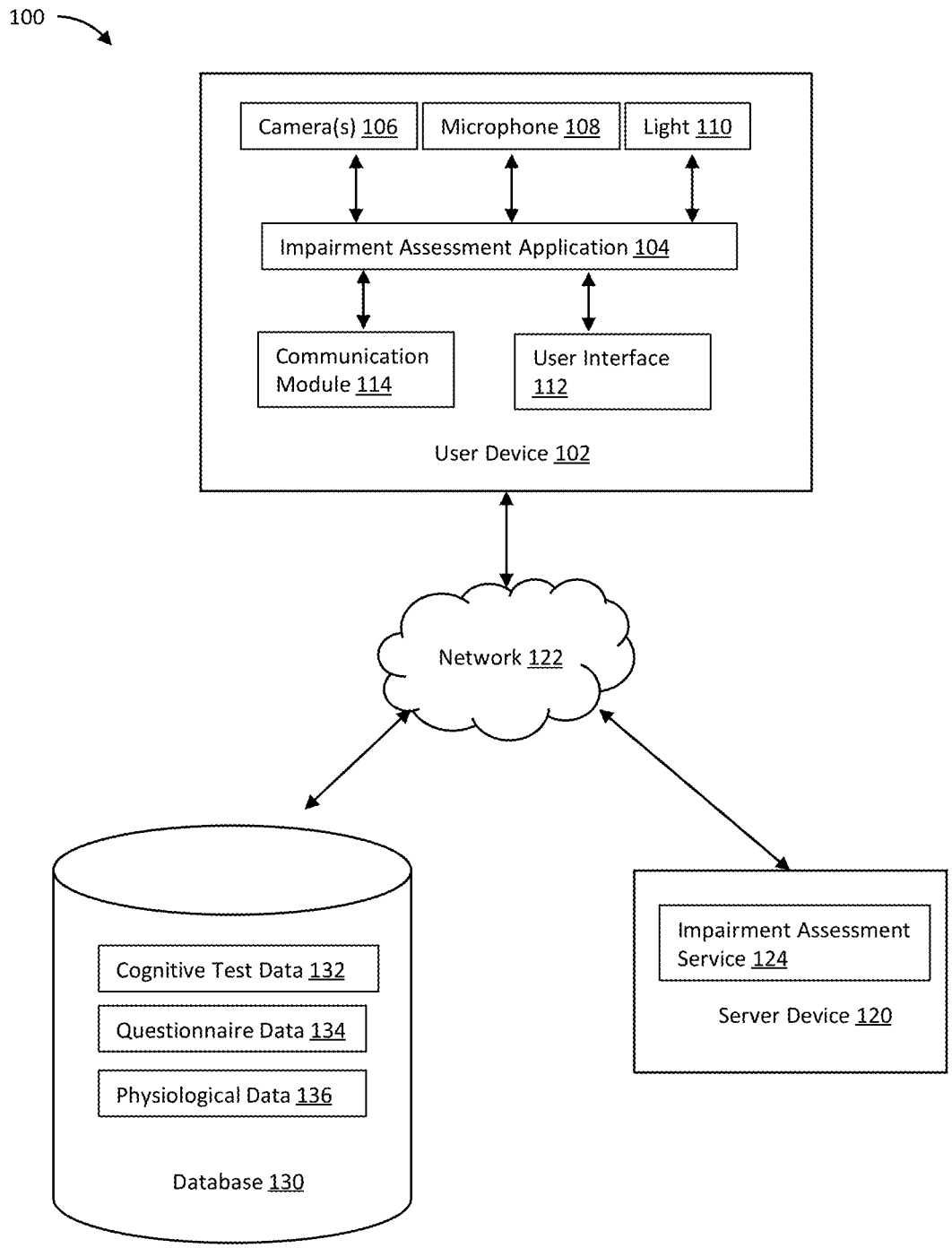
FIG. 1 is a block diagram of an example impairment assessment system.

FIG. 1 is a block diagram of an example system 100 for rapidly and non-invasively assessing the presence or absence of a neurocognitive, physiological and/or behavioral impairment of a user due to the ingestion of a substance. A cognitive impairment or cognitive effect can be any neurological effect caused by a substance and system 100 may be configured to test for the impairment of any cognitive aptitude known in the art. Non-limiting examples of cognitive aptitudes that system 100 may be configured to test include any aptitude associated with intellectual capacity, attention and concentration, processing speed, language and communication, visual-spatial abilities, and memory. In some examples, system 100 may be configured to test for the impairment of one or more of sustained attention, sense of timing, psychomotor control, short term memory, working memory, spatial reasoning, divided attention, response inhibition, creativity, and risk taking, among others. System 100 may be configured to test for cognitive impairment generally or cognitive impairment due to the ingestion of one or more particular substances, such as alcohol, cannabis, opioids, and/or benzodiazepines, among others. System 100 may also be configured to assess a user's subjective experience due to the ingestion of a substance by presenting one or more user-input questionnaires including a user's perceived mood, behavior, energy level, level of concentration and perceived degree of cognitive impairment. System 100 may also be configured to receive physiological sensor data measurements for features of a user's face, eyes, speech or voice, motor control and dexterity, and other physiological measurements such as heart and respiratory rate that may be used to assess the presence of physiological effects caused by a substance.

System 100 includes at least one user device 102 configured to execute an impairment assessment application 104 for assessing behavioral-neuro-physiological characteristics of a user. User device 102 is a computing device and may be any of a variety of computing devices, such as a smartphone, tablet computer, laptop computer, smart watch, smart glasses, etc. In other examples, as opposed to a general purpose computer, user device 102 may be an electronic device specifically designed for providing an impairment assessment, such as a device specifically designed for roadside, home, and/or dispensary use including a specially designed housing and hardware. In the illustrated example, user device 102 includes or is otherwise operably coupled to one or more image capture devices (cameras) 106 for capturing still or moving images of a user's body and face, a microphone 108 for recording a user's speech, and one or more light sources 110 for providing visible and non-visible, such as infrared radiation for illuminating, e.g., the user's face or the user's skin, for example, for eye measurements and to detect heart rate. Any type of camera, microphone, and light may be utilized, including cameras, microphones and light sources typically found on consumer electronic devices such as smart phones and laptops. Any of a variety of additional smart device sensors that may be utilized to capture information included in a physiological assessment, including blood pressure, respiratory rate, and pulse oximeter sensors, among others.

User device 102 may also include a user interface 112 which may have any feature of user interfaces known in the art, including a display screen for providing a graphical user interface including a touch and pressure-sensitive display for displaying graphical user control elements, receiving user control inputs and measuring a pressure of a user's touch on the display, and one or more hard controls, such as buttons, switches, dials, etc. for receiving user controls. User device 102 may also include a communication module 114 for wired and/or wireless communication with one or more other computing devices.

In the illustrated example, user device 102 is configured to communicate with a server device 120 over a network 122, the server device configured to provide an impairment assessment service 124 to any number of end users via user computing devices such as computing device 102. Impairment assessment application 104 may include various circuits, circuitry and one or more software components, programs, applications, or other units of code base or instructions configured to be executed by one or more processors included in user device 102 or server device 120. In some examples, one or more modules or components of impairment assessment application 104 may be included in user device 102 with other modules or components included in server device 120. In some examples, impairment assessment application 104 may be configured to collect user data from one or more of cognitive assessment tests, physiological tests, and/or user subjective input and some or all of the collected data may be processed by impairment assessment service 124. In some examples, system 100 includes a database 130 in communication with user device 102 and server device 120 that may receive and store data collected by user device 102 and provide datasets collected over time from user performance data that may be used to provide a cognitive impairment assessment for a user. In the illustrated example, database 130 may include cognitive test data 132 that may include data associated with one or more cognitive tests that, as described below test cognitive and behavioral characteristics of a user; questionnaire data 134 that may include user responses to questionnaires, for example, presented in conjunction with the presentation of cognitive tests, and physiological data 136 that may include physiological sensor data collected and analyzed in conjunction with the presentation of cognitive tests.

In some examples, impairment assessment service 124 may be configured to leverage both supervised and unsupervised artificial intelligence and classification and clustering methods to determine both the presentation (sequencing and instances) of items such as games, tasks, and subjective questions as well as analysis of the user's general performance and impairment assessment. Artificial intelligence, classification, and clustering methods may include but are not limited to: logistic regression, decision trees, and neural network models in which previously captured/collected or existing individual user information and also aggregate or larger scale, multi-user information is utilized in the analysis of a particular user's performance or group of users performance throughout the application or for other information captured such as physiological features and measurements to provide results such as impaired/not impaired or differentiation between substances.

In one example, impairment assessment application 104 and/or impairment assessment service 124 may be configured to execute logistic regression algorithms and models for analyzing multiple variables to assist in the determination of what substances and doses effect specific neurocognitive physiological and subjective domains for individual users and aggregate users.

In another example, decision trees may be utilized to classify information collecting by dividing previous information collected into numerous smaller subsets, each determined by specific user inputs or patterns of inputs.

In yet another example, a neural network artificial intelligence model may be utilized to identify and weight specific inputs provided by users to determine a specific output such as present a new task (e.g. new cognitive test 302), repeat a task (e.g., repeat the same cognitive test 302 as just presented), present the user with one or more questions to illicit subjective information, etc. The weighted activities and inputs may be included in a presentation of items and in a performance assessment analysis.

In some examples, impairment assessment service 124 may be configured to execute one or more machine learning algorithms which may include one or more models that may utilize training instances to provide a cognitive impairment assessment for a user. Machine learning broadly refers to utilizing algorithms to learn from data and identify and compare patterns in data. A variety of different types of machine learning techniques may be employed in embodiments of the present disclosure. Non-limiting examples of machine learning techniques that may be employed include decision tree and association rule learning, supervised, unsupervised, or semi-supervised learning, and classification, regression, and clustering techniques, among others. One example implementation utilizes supervised classifier machine learning models and algorithms. In some examples, supervised learning models utilizing Support Vector Machines (SVM) may be used. As will be appreciated, these models are merely provided by way of example and other machine learning techniques may also be utilized to provide a digital impairment assessment in accordance with the present disclosure.

Impairment assessment service 124 may be configured to learn from cognitive test data 132, questionnaire data 134, and physiological data 136 to train one or more classifiers and learn from the data. Impairment assessment service 124 may be configured to provide an impairment assessment based on the machine learning classifiers that, in some examples, are continuously updated with information as data from new tests performed by user devices such as user device 102 are received. In some examples, database 130 may receive training data from situations where the type and amount of substance consumed is known. For example, controlled laboratory experiments and when users such as individuals or dispensaries input the type and amount of substance which may be stored in database 130 in combination with the results of cognitive testing. Impairment assessment service 124 may be configured to continuously adapt to new training instances to provide a cognitive impairment assessment, including in cases where the type and substance has not been provided, such as in a roadside law enforcement application or employee testing application. Impairment assessment service 124 may be configured to provide a variety of analyses, such as likelihood of cognitive impairment above a predefined threshold such as a legal limit of intoxication for safe motor vehicle operation and type of substance(s) causing a detected cognitive impairment.

In some examples, network 122 may include one or more of a local area network, wide area network, the Internet, a direct peer-to-peer network, an indirect peer-to-peer network (e.g., devices communicating through a server, router, or other network device) etc. Network 122 may be a single network or multiple networks. For example, user device 102 and one or more of camera 106, microphone 108 and light source 110 may communicate through a direct peer-to-peer network while user device 102 and server device 120 may communicate through the Internet. Network 122 may be configured for any wired or wireless communication protocol known in the art.

Figure 2:
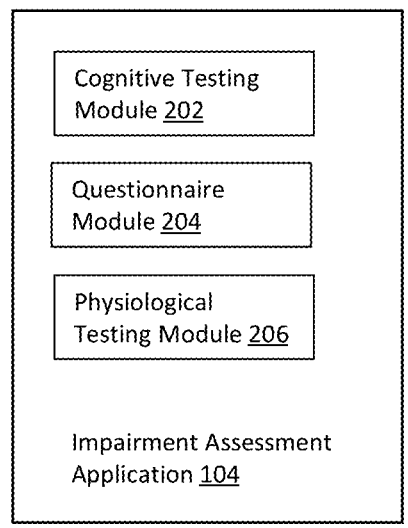
FIG. 2 is a functional block diagram of portions of one example implementation of an impairment assessment application.

FIG. 2 shows a functional block diagram of portions of one example implementation of impairment assessment application 104 and includes a cognitive testing module 202, a questionnaire module 204 and a physiological testing module 206. One or more components of any of modules 202-206 may be executed by a processor on user device 102 while one or more other components may be executed by a processor of server device 120. In one example implementation, impairment assessment service 124 is configured as a software-as-a-service (SaaS) application with impairment assessment application primarily executed by server device 120 through a web browser or other graphical user interface on user device 102. In some implementations, impairment assessment application may include only two or one of modules 202-206. For example, an impairment assessment application 104 for roadside law enforcement applications may only include one or both of cognitive testing module 202 and physiological testing module 206 while an impairment assessment application 104 for use by a dispensary or home use, for example, for determining a proper dosage amount of a substance may include each of cognitive testing module 202, questionnaire module 204 and physiological testing module 206, or only cognitive testing module 202 and questionnaire module 204.

Figure 3:
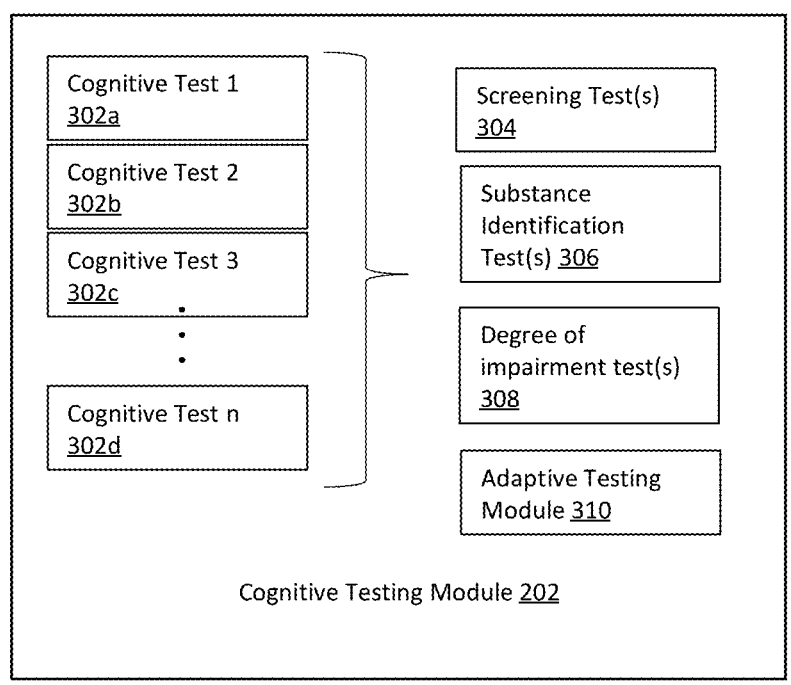
FIG. 3 is a functional block diagram of one example implementation of a cognitive testing module configured to execute one or more of a plurality of cognitive tests.

FIG. 3 illustrates a functional block diagram of one example implementation of cognitive testing module 202. In the illustrated example, cognitive testing module includes a plurality of cognitive tests 302a, 302b, 302c . . . 302n that are designed and configured to assess one or more of cognitive, neurocognitive, and/or behavioral characteristics of a user and in some examples designed and configured to test one or more specific cognitive aptitudes in order to determine characteristics of a cognitive impairment or attribute of a user. In one example, one or more of cognitive tests 302 are designed and configured as a game configured to be displayed on user interface 112 of user device 102 and be played by a user via user control elements of user interface 112. Non-limiting examples of cognitive aptitudes that cognitive tests 302 may be configured to test include any aptitude associated with intellectual capacity, attention and concentration, processing speed, language and communication, visual-spatial abilities, and memory. In some examples, system 100 may be configured to test for the impairment of one or more of sustained attention, sense of timing, psychomotor control, short term memory, working memory, spatial reasoning, divided attention, response inhibition, creativity, and risk taking, among others. System 100 may also be configured to test for and detect people having above-average abilities in any of the cognitive aptitudes described herein.

In one implementation, cognitive testing module 202 also includes a screening test module 304, a substance identification test module 306, a degree of impairment test module 308 and an adaptive testing module 310. In one implementation, each of modules 304-310 may pull from and select one or more of cognitive tests 302 depending on the particular function or operation being performed. For example, in one implementation, screening test module may be called to present one or more of cognitive tests 302 as screening tests, for example, to obtain an initial assessment of likelihood of impairment and/or an identification of a substance that is likely causing impairment. Adaptive testing module 310 may be configured to vary a selection and sequence of cognitive tests 302 according to the results of one or more initial tests presented by screening test module 304. Substance identification test module 306 may include one or more of cognitive tests 302 that are designed and configured to test specific combinations of cognitive aptitudes to determine a likely substance that was ingested and is causing a neurological impairment. For example, different substances such as alcohol, cannabis, opioids, and/or benzodiazepines, among others affect different combinations of particular cognitive aptitudes and to differing extents. Substance identification testing module may be configured to systematically test combinations of cognitive aptitudes to arrive at a determination of a likely substance that is causing a cognitive impairment.

Degree of impairment test module 306 may include one or more of cognitive tests 302 that are designed and configured to determine a likely degree of neurological impairment and/or degree of above-average neurological capabilities. In some examples, degree of impairment test module 306 is not specific to a particular substance and instead tests a specific selection of cognitive aptitudes considered necessary for safe motor vehicle and general equipment operation to determine if a user capabilities are impaired to the extent that it would be unsafe for him or her to operate a motor vehicle or, conversely, if the user has above average capabilities indicating he or she would be a good candidate for a position involving the operation of a motor vehicle. In other examples, degree of impairment test module 306 may be substance specific, for example, be configured to present a first selection and sequence of cognitive tests 302 when a user has ingested a first substance or combination of substances and a second selection and sequence of cognitive tests 302 when a user has ingested a second substance or combination of substances. For example, degree of impairment test module 306 may be configured to specifically test for and determine a degree of cognitive impairment of a user that has ingested a cannabis product to determine if the user is legally intoxicated and has a cognitive impairment above a legal limit for safe motor vehicle operation. Similarly, degree of impairment test module 306 may be configured to specifically test for and determine a degree of cognitive impairment of user that has ingested a psychomotor stimulant, alcohol, or an opioid.

In one example, cognitive testing module 202 may be configured to execute screening test module 304 to determine a likely type of substance that is causing cognitive impairment and then execute degree of impairment test module 308, wherein the selection and sequence of cognitive tests 302 executed by degree of impairment test module 308 is determined according to user performance data collected during execution of the screening test module.

Adaptive testing module 310 may be configured to vary a selection and sequence of presentation of cognitive tests 302 according to a user's performance, for example, during execution of any of modules 304-308 or during execution of cognitive tests 302. In one example, any one or more of the modules of cognitive testing module 202 may be configured with one or more machine learning algorithms including any of the types of machine learning algorithms described herein for comparing user performance data to data in database 130 and/or one or more training datasets and classifiers to provide a determination, for example, a determination of a likely substance(s) that is causing impairment, a likelihood of impairment, a degree of impairment, and/or a likelihood an impairment is above a threshold value, such as a legal limit for operation of a motor vehicle or a target limit for a particular unit dosage of a substance. For example, a myriad of performance data may be collected during the performance of each cognitive test 302 which may be compared to large datasets in database 130 for providing a cognitive impairment assessment.

Figure 4:
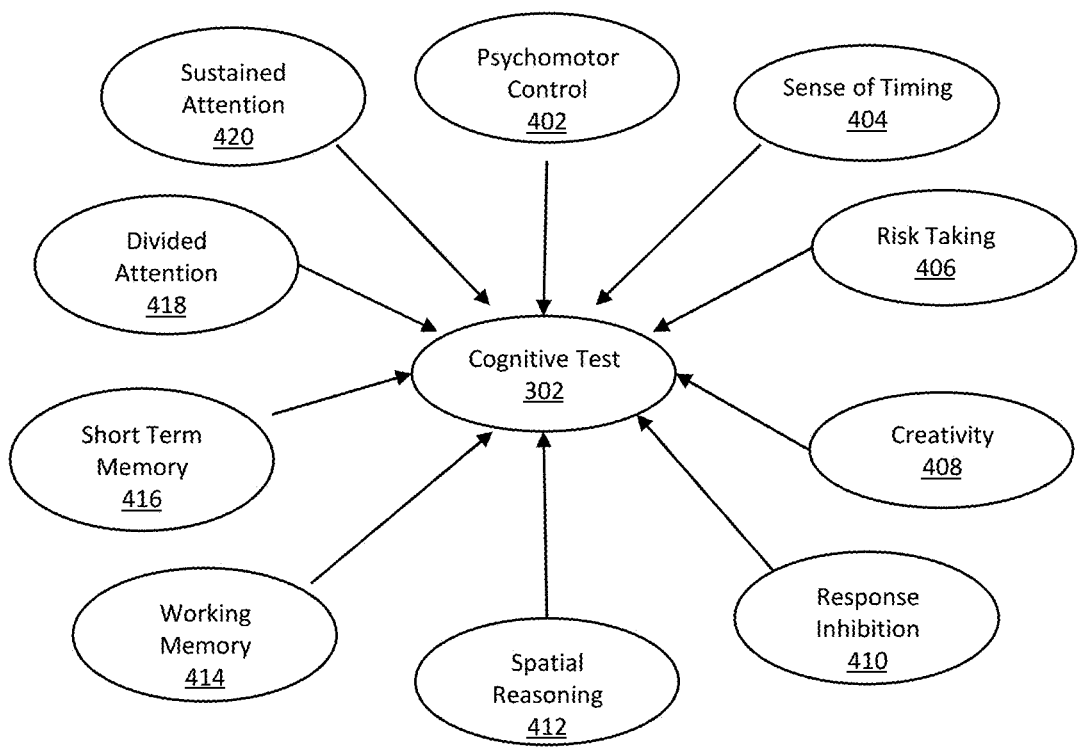

FIG. 4 illustrates examples of cognitive aptitudes 400, particular combinations of which cognitive tests 302 may be designed to test for. As shown in FIG. 4 example cognitive aptitudes that may be impaired by substances and that may be relevant for differentiating between substances and determining a degree of impairment include psychomotor control 402, sense of timing 404, risk taking 406, creativity 408, response inhibition 410, spatial reasoning 412, working memory 414, short term memory 416, divided attention 418, and sustained attention 420. The illustrated cognitive aptitudes are shown by way of example and systems made in accordance with the present disclosure may test for others not listed. In one example, each of cognitive tests 302 are designed as games configured to be displayed on user interface 112 of user device 102 and are designed and configured to test one or more of cognitive aptitudes 400. Cognitive testing module 202 may be configured to collect user performance data for each of the cognitive aptitudes 400 and store the user performance data in a database, e.g., database 130.

Systems made in accordance with the present disclosure may include any number of cognitive tests 302 designed to test any of a variety of cognitive aptitudes 400. In some examples, cognitive testing module 202 may include a collection of cognitive tests 302 and may not present all tests to each user. For example, a subset of tests 302 may be presented according to, for example, a user selected testing function and/or user performance data from initial tests, such as during execution of screening testing module 304. By way of non-limiting example, in one implementation cognitive tests 302 may include a first cognitive test 302a in the form of a game that tests psychomotor control 402 including psychomotor compensation and sustained attention 420; a second cognitive test 302b in the form of a game that tests a sense of timing 404 by testing the ability to observe and recall a randomly presented timing of an event, response inhibition 410, and sustained attention 420; a third cognitive test 302c in the form of a game that tests sustained attention 420, divided attention 418, and short term memory 416; a fourth cognitive test 302d in the form of a game that tests psychomotor control 402 in the form of reaction time, and response inhibition 410; a fifth cognitive test 302e in the form of a game that tests psychomotor control 402 and divided attention 418; a sixth cognitive test 302f in the form of a game that tests psychomotor control 402, short term memory 416, working memory 414, and sustained attention 420; a seventh cognitive test 302g in the form of a game that tests short term memory 416, sustained attention 420, and risk taking; an eighth cognitive test 302h in the form of a game that tests spatial reasoning 412 and working memory 414; a ninth cognitive test 302i in the form of a game that tests spatial reasoning 412 and creativity 408; and a tenth cognitive test 302j in the form of a game that tests psychomotor control 402 including reaction time and response inhibition 410. As will be appreciated, the foregoing list of ten cognitive tests 302 are merely provided by way of example and cognitive testing module may include other cognitive tests 302 that test other combinations of cognitive aptitudes, including any combination of cognitive aptitudes 400.

Example Cognitive Tests

Figure 5:
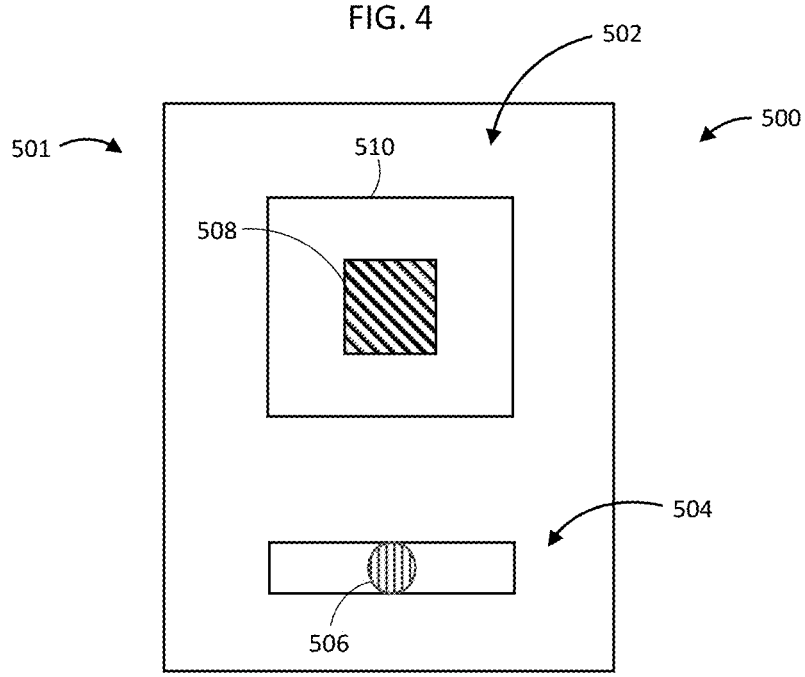
FIG. 5 shows a graphical user interface (GUI) for one example cognitive test that is designed and configured to test at least psychomotor compensation and sustained attention.

The present disclosure provides illustrations and an accompanying description of examples of cognitive tests that may be included in cognitive testing module 202. The illustrated examples are merely provided by way of example and modifications may be made and other tests included that test alternate combinations of cognitive aptitudes, including the examples of cognitive aptitudes illustrated in FIG. 4 and otherwise described herein. FIG. 5 illustrates a graphical user interface (GUI) 501 for one example cognitive test 500 that is designed and configured to test at least psychomotor control 402 (FIG. 4) including psychomotor compensation as well as sustained attention 420. Cognitive test 500 is an example of one of cognitive tests 302 (FIG. 3). GUI 501 may be displayed on a display screen of user interface 112 of user device 102 and includes a display portion 502 and a user control element portion 504 including a lateral control element 506 that, in the illustrated example is a soft control element displayed graphically on a touch sensitive display. In the illustrated example, the user is instructed to use lateral control element 506 to maintain object 508 within target area 510. Software instructions for cognitive test 500 may include instructions for periodically, and in some examples randomly, moving object 508 in a first direction, for example left, right, up, down or any other linear or non-linear direction and path, and the user is instructed to move lateral control element in the opposite direction to maintain the object in target area 510. In one example, cognitive test 501 may include instructions for moving object 508 erratically and for measuring the accuracy and speed of psychomotor compensation by the user according to the user's ability to maintain object 508 in target area 10. Cognitive test may also include instructions to instruct the user to keep his or her finger on lateral control element 506 and monitor whether the user fails to maintain contact and lift his or her finger away.

Cognitive test 501 assesses accuracy and speed of psychomotor compensation which is a skill that may be considered relevant for determining a user's ability to safely operate a motor vehicle, for example, is analogous to a driver adjusting steering to compensate for the occurrence of ice on the pavement. Cognitive test 501 can be presented in many alternate forms from the example shown in FIG. 5 but that include a user required to manipulate an object in the foreground while adjusting for changes to the background.

Figure 6A:
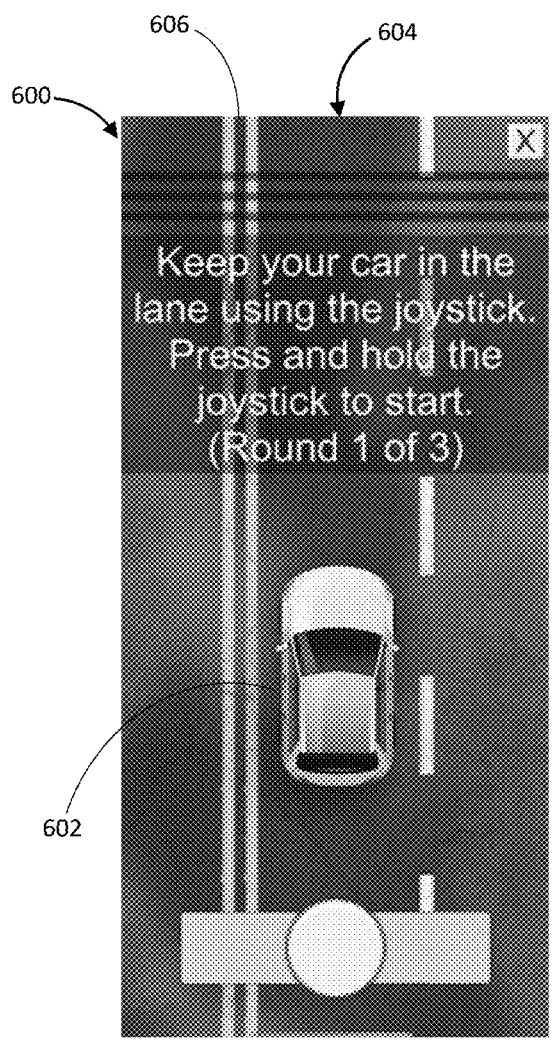
FIGS. 6A-6D show a GUI for one example cognitive test that is designed and configured to test at least psychomotor compensation and sustained attention.
Figure 6B:
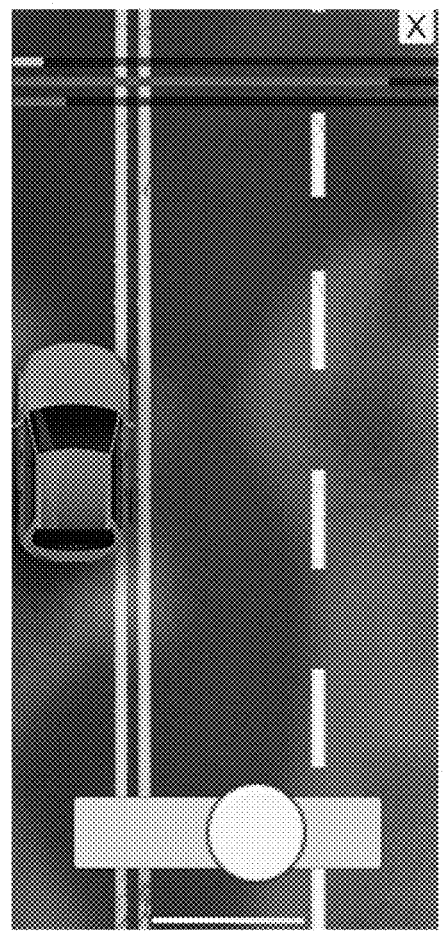
Figure 6C:
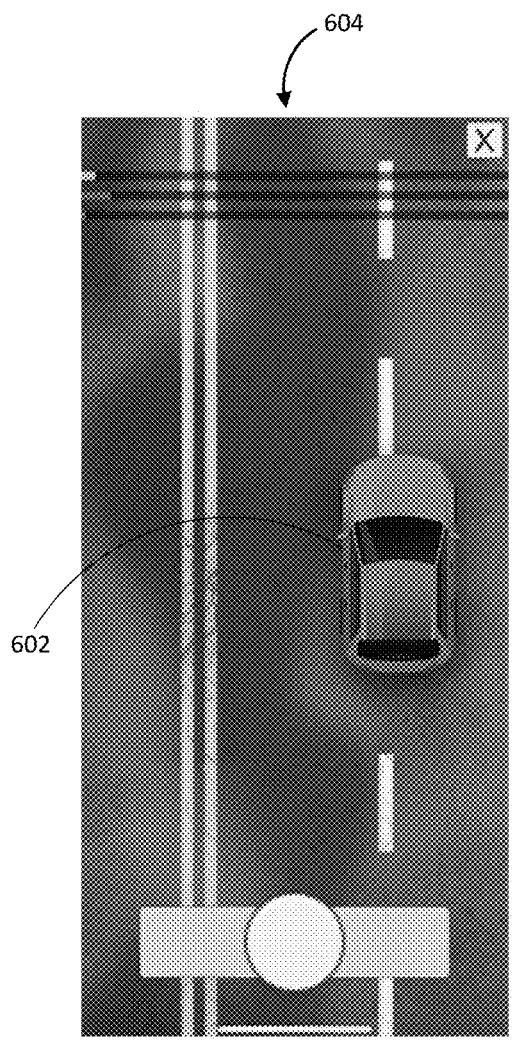
Figure 6D:
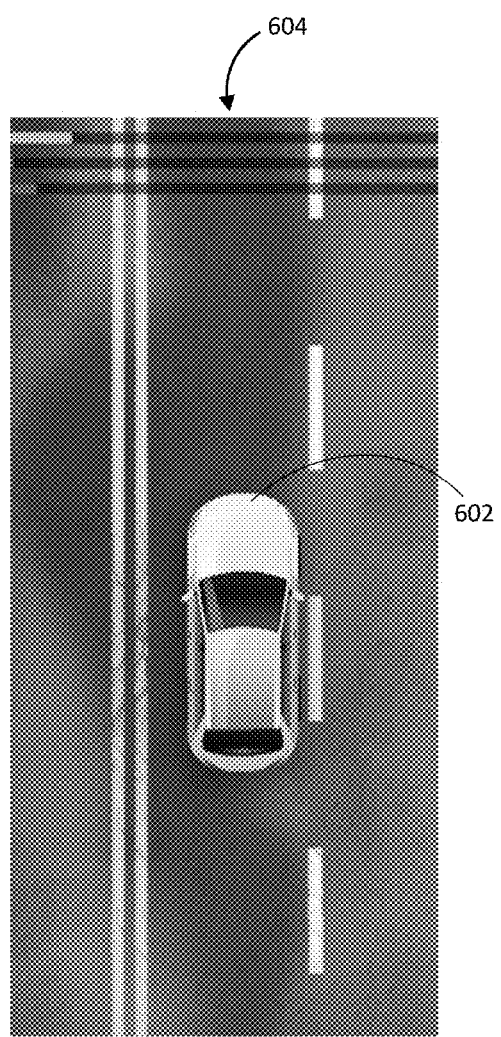
Figure 7A:
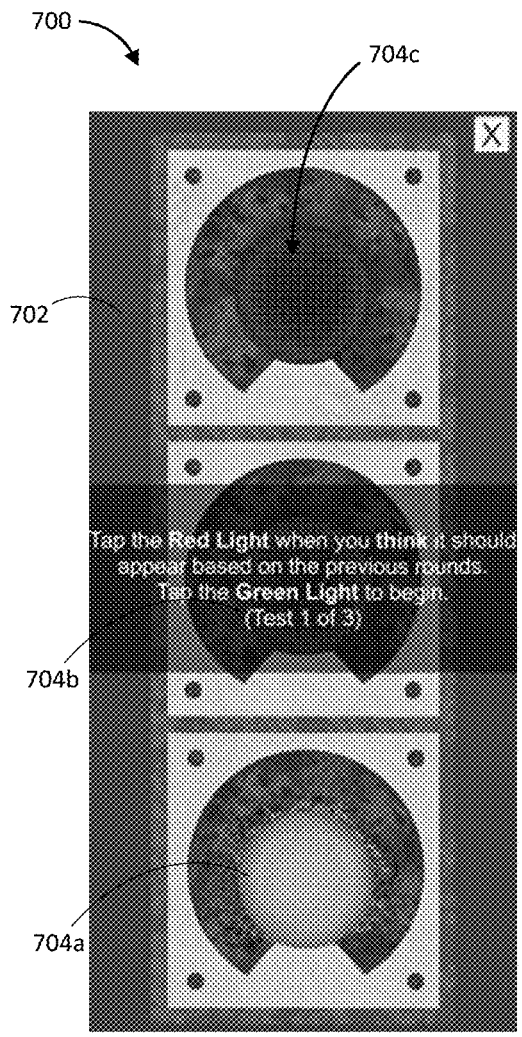
FIGS. 7A-7D show a GUI for one example cognitive test that is designed and configured to test at least a user's sense of timing.
Figure 7B:
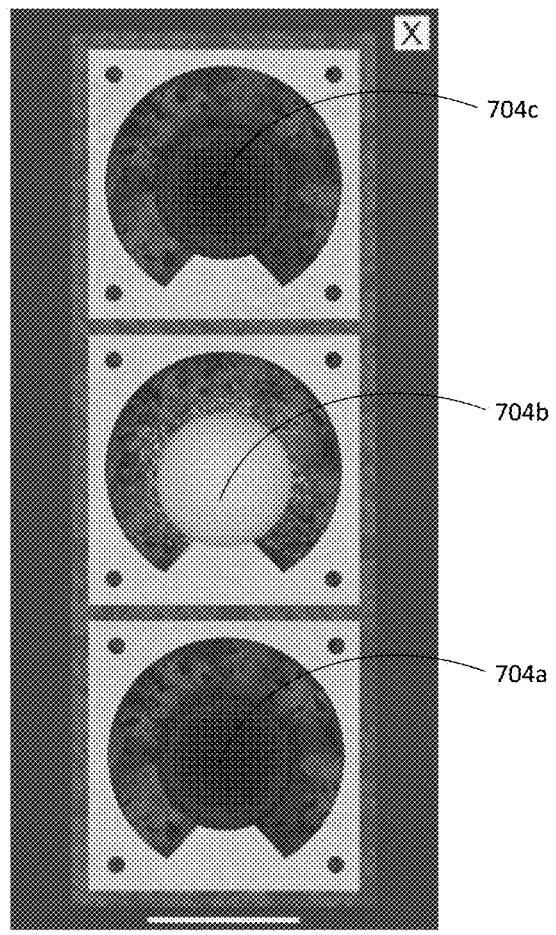
Figure 7C:
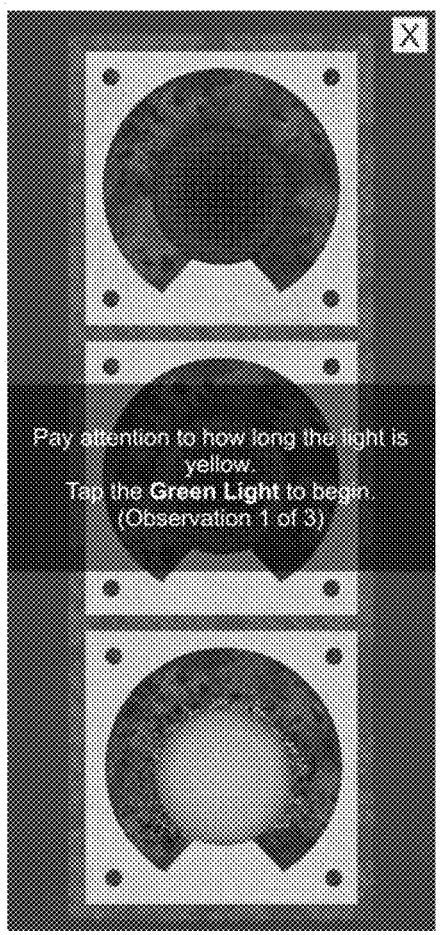
Figure 7D:
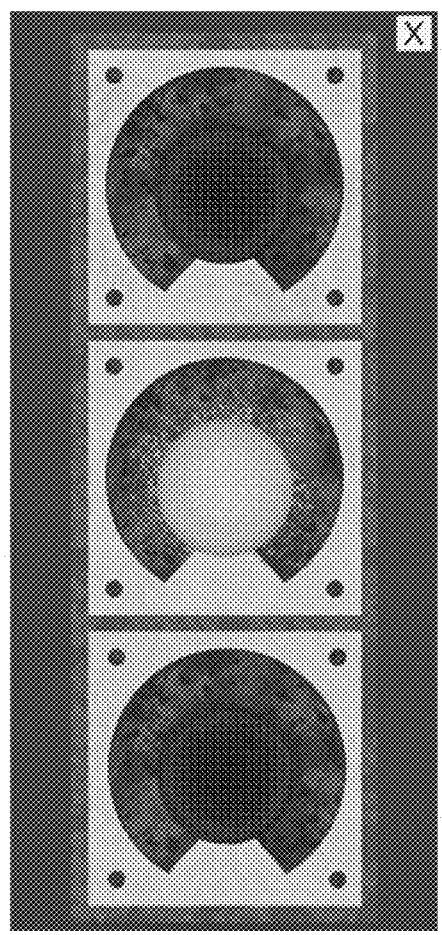

FIGS. 6A-6D illustrate one example implementation of cognitive test 500 in the form of cognitive test 600 that includes a GUI that is configured to display a bird's-eye view of a motor vehicle in the form of a car 602, the user required to maintain the car in the lane 604 and to the right of the double yellow line 606 and compensate for the car's erratic movement on the pavement (background). In one example, the movement of the foreground object, car 602, becomes more erratic over time, making the task more difficult. FIG. 6B shows car 602 outside of lane 604, the car has changed color indicating the car is outside the lane, FIG. 6C similarly shows the car outside of the lane and a changed color, and FIG. 6D shows the car back inside the lane and the color reverted to the first color also shown in FIG. 6A. Instructions for the game may include: "Keep your finger on the joystick to drag the car in the direction you want it to move. Try to keep the car in the center of the lane, on your side of the street." Cognitive test 600 may be configured to collect a variety of user performance data. For example, user performance data may include one or more of (A) time to failure, which in one example may be the primary dependent variable. Time to failure may be calculated as a maximum summed duration the user keeps the car in the lane out of a total possible allotted time for play. Other user performance data may include (B) rate of improvement over the course of successive trials; (C) instruction omission in the form of the number of times the user lifts his finger off of control element 506 despite being instructed to maintain contact; (D) frequency of compensation failures when the user is operating control element 506 counterproductively, for example, when the user should be moving the car 602 toward the center of lane 604, his or her action is the opposite, pushing the car outside of the lane. In one example, a data processing formula for calculating a performance metric from the four preceding performance data may be: B (1-A)+(N*C)+(V*D), where N and V are empirically derived multipliers. In other examples, additional performance data may also be collected.

FIGS. 7A-7D illustrate another example cognitive test 700 that includes a GUI 702 that may be displayed on a display screen of user interface 112 of user device 102 and includes a display portion that includes a plurality of touch sensitive color-changing elements 704a, 704b, 704c. Cognitive test 700 is an example of one of cognitive tests 302 (FIG. 3). In the illustrated example, the color changing elements are modeled after a traffic light and each is configured to turn on and off by transitioning between a dark color and green (color changing element 704a), yellow (color changing element 704b), or red (color changing element 704c). The color changing elements 704 turn on and off at various time intervals, and in one example, the time intervals are randomized from one trial of the game to the next.

In one example the user is required to assess the timing of when the color changing elements 704 turn on as they occur in relation to each other and then predict a subsequent occurrence, e.g., when a particular color changing element 704 will come on after another one has turned on. The user may be instructed to press the color changing element 704 when he thinks it should turn on. In one example the user may be instructed to assess the timing of the switching on-and-off from green to yellow to red. The user may be instructed to estimate the timing of the transition in color and position by then pressing the color changing elements in a particular order and timing after observing one or more example sequences. In one example, between gaming experiences, the timing sequence is randomized such that on the first occasion, the user may have to estimate 2.2 s, but on the next occasion, 4.1 seconds. In one example, the array of values used to present the stimuli (color changing elements 704) only include non-whole integers, for example, not an even 2.0, 3.0, or 4.0 seconds, to prevent a user from cheating by using a timing device, such as a watch to measure and then repeat a time duration. In one example, instructions for the training may include: "Tap the green light. Pay attention to how long the light is yellow." Testing instructions may include: "Tap the green light, then tap the red bulb when you think it will light red, based on the previous examples." Examples of performance data collected by cognitive test 700 include timing (e.g. in msec) between the "green/bottom touch (e.g.)" and the "red/top touch" which may be used to calculate proportionate error per occasion, for example: ABS(performance—timing value)/timing value.

Cognitive test 700 is an example of a randomized short term differential reinforcement of low rate (DRL) test and is configured to measure a user's ability to observe and accurately recall specifically timed events by touching the screen of the device. Cognitive test 700 may test cognitive aptitudes including sense of timing 404 (FIG. 4) by testing the ability to observe and recall a randomly presented timing of an event, as well as response inhibition 410, and sustained attention 420.

In one example, cognitive test 700 may be included in screening test module 304 and/or substance identification test module 306 because different substances have differing impacts on an individual's sense of timing. For example, an individual's sense of timing is interrupted in different ways by stimulants versus cannabis, and is not impaired as much by alcohol as compared to cannabis. Accordingly, cognitive testing module 202 may be designed and configured to determine one or more of a selection of cognitive tests 302 and a sequence of the tests according to how a user performs when playing cognitive test 700. For example if user performance data from cognitive test 700 indicates an impaired sense of timing, that is an indication that the user is suffering from a cognitive impairment caused by cannabis and impairment assessment application 104 may be configured to select one or more additional cognitive tests designed and configured to test for cannabis-caused cognitive impairment for presentation to a user following the execution of cognitive test 700. In one example, if user performance data indicates a user's performance on cognitive test 700 is poor and the user's results generally underpredict a time duration (the user consistently presses color changing elements 704 too soon) that may be an indication the user is suffering from a cognitive impairment caused by a psychomotor stimulant. In one example, after detecting the possible presence of a psychomotor stimulant, cognitive testing module 202 may be configured to select one or both of cognitive tests 1000 and 1100 (described more below) for automatic execution and presentation to the user after cognitive test 700 to further assess the presence of a stimulant because stimulants impact response inhibition 410 more so than other substances. In another example, if user performance data indicates a user's performance on cognitive test 700 is poor and that the user's error varies between the user's results underpredicting and overpredicting or in another example, if the user both under and overpredicts and/or the user consistently overpredicts the time duration (the user presses color changing elements 704 both too soon and too late or consistently presses too late) that may be an indication the user is suffering from a cognitive impairment caused by cannabis. In one example, after detecting the possible presence of cannabis, cognitive testing module 202 may be configured to select and automatically execute one or more of cognitive tests 500, 600, 800, and 900 to further assess the presence of cannabis and degree of cannabis impairment because, among other cognitive aptitudes, cannabis impacts sustained attention 420, short-term memory 416, and divided attention 418, which are important cognitive aptitudes for safe motor vehicle and equipment operation.

Figure 8A:
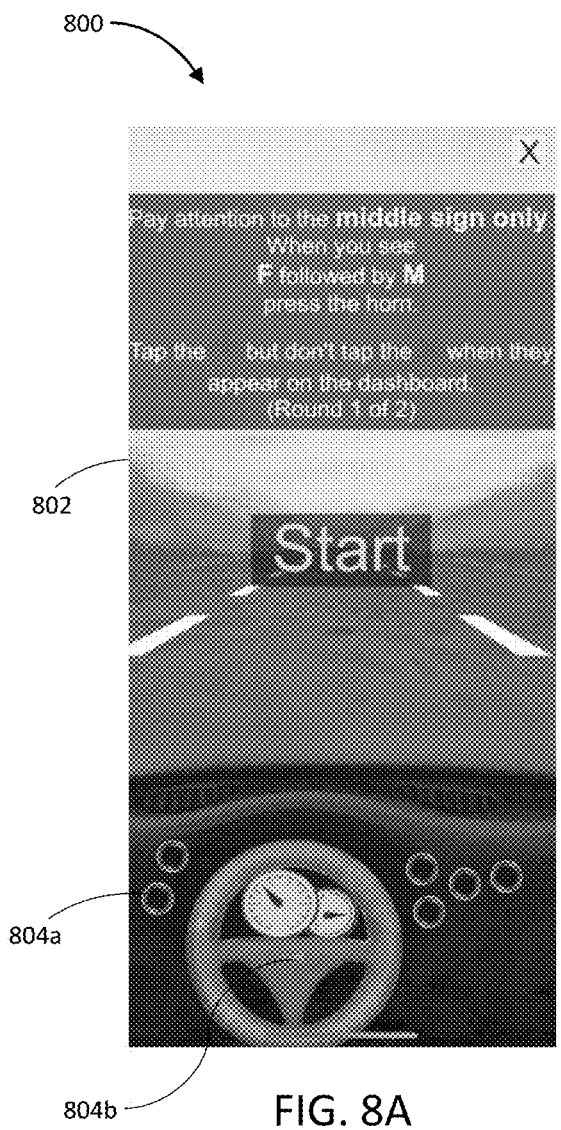
FIGS. 8A-8D show a GUI for one example cognitive test that is designed and configured to test at least sustained attention, short-term memory, and divided attention.
Figure 8B:
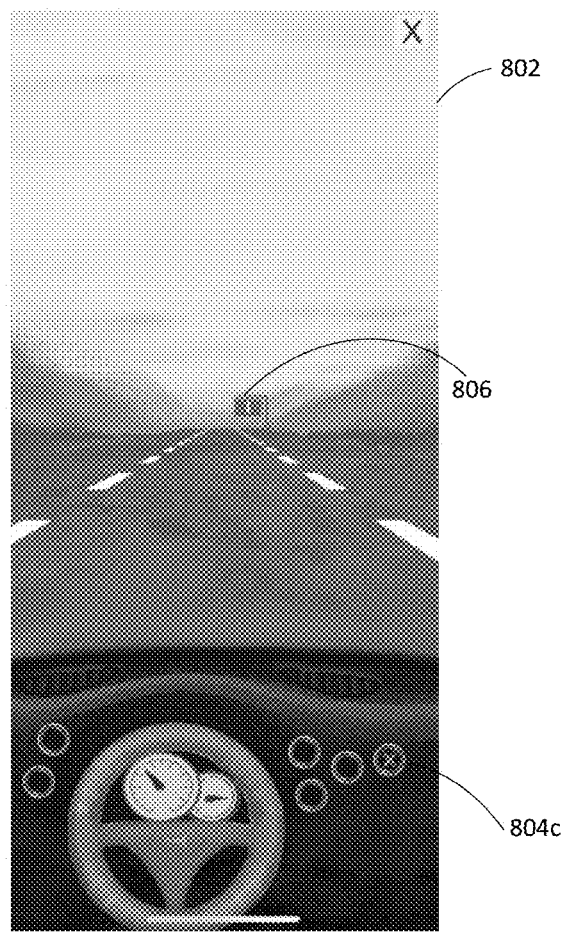
Figure 8C:
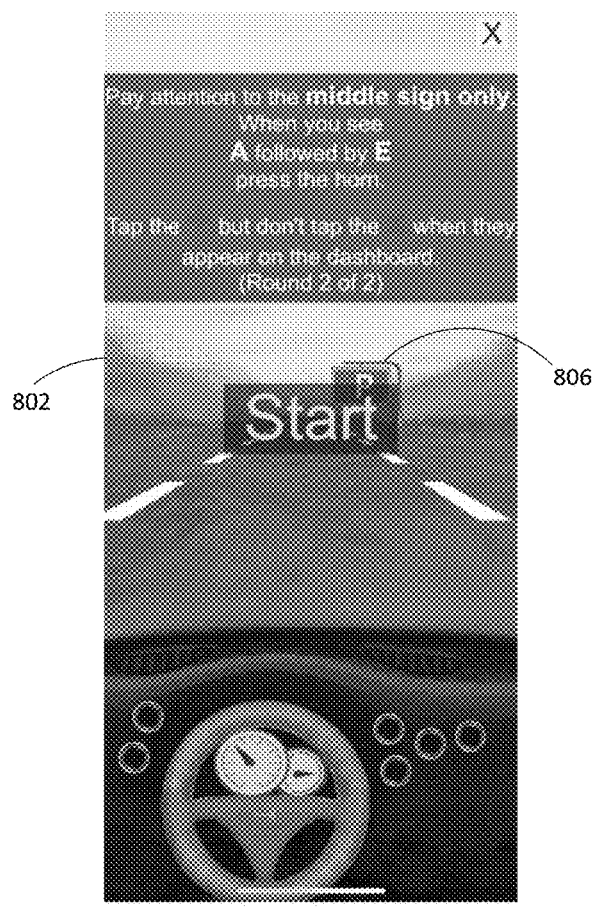
Figure 8D:
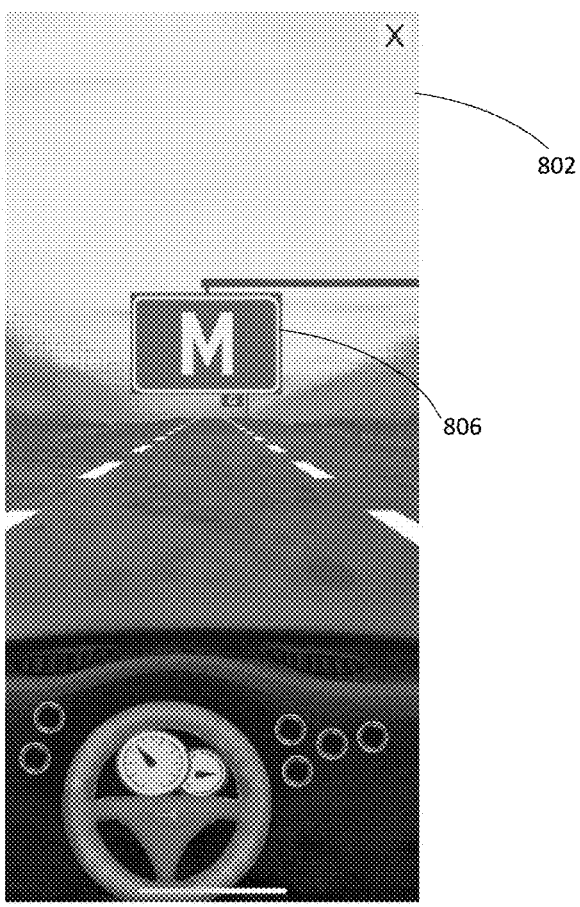

FIGS. 8A-8D illustrate another example cognitive test 800 that includes a GUI 802 that may be displayed on a display screen of user interface 112 of user device 102 and includes a display portion that includes a plurality of touch sensitive control elements, for example, touch sensitive control elements 804a, 804b, and 804c. Cognitive test 800 is an example of one of cognitive tests 302 (FIG. 3). In the illustrated example, GUI 802 is configured to display a first display portion that shows the interior of a motor vehicle from the perspective of the operator and a second display portion that includes a road and surrounding environment. During execution of the test, the road and surrounding environment move relative to the vehicle interior to give the illusion of movement and stimuli in the form of road signs 806 begin to appear. In one example, the user is instructed that a plurality, e.g., three road signs 806 will be presented, to pay attention to the middle road sign, and when a second symbol, e.g., 'Z' appears after a first symbol, e.g., 'Y', tap the 'HORN' (control element 804b). FIGS. 8B-8D show one example where road signs 806 displaying differing symbols (here a letter I, P, M, and G) are sequentially displayed and the road signs progress in a downward direction while increasing in size at a given rate to create the illusion of approaching signs. In one example, the rate of movement of road signs 806 can be increased to increase a level of difficulty. Example test 800 tests sustained attention 420 and short-term memory 416 by requiring the user to remember the particular sequence of symbols and requiring the user to maintain attention as various road signs 806 appear.

In one example, cognitive test may also instruct the user to not only monitor the symbols displayed on road signs 806 in the first display portion of GUI 802 but also monitor user control elements 804a and 804c in the second display portion of the GUI and tap those control elements when a first symbol appears, e.g., a + but not when a second symbol appears, e.g., an X. FIG. 8B shows an example where an X is displayed. The monitoring of both the first and second display portions and the concurrent performance of two tasks (here, monitoring for a particular sequence of symbols on road signs 806 and monitoring for a particular symbol in the second display portion) is an example test of divided attention 418 (FIG. 4). Thus, cognitive test 800 is designed to test targeted and distracted attention to measure a user's ability to respond to target stimuli when presented with and without additional tasks to complete simultaneously and assesses (a) attention to detailed instructions, (b) sustained attention, and (c) divided attention. In one example, training instructions may be: "Three road signs will be presented at a time. Pay attention to the middle road sign, and when a 'Z' appears after 'Y', tap the 'HORN'. In one example, testing instructions may include: "The task is going to get more difficult. Again, three road signs will be presented at a time. Pay attention to the middle road sign, and when a 'Y' appears after 'Z', tap the 'HORN'. ALSO, on the edges of the screen, you will see + and x appear. When you see '+', tap it."

Impairment assessment application 104 and impairment assessment service 124 may be configured to collect and process a variety of user performance data from cognitive test 800. Non-limiting examples of user performance data include a number of omissions calculated, for example, a first omission type for the number or percent of occasions the target sequence was presented but the user failed to recognize the occurrence and press user control element 804b prior to the presentation of the next three-character sequence, and a second omission type for the number or percent of occasions when the target symbol in the second display portion, e.g., the + on the dashboard, was presented but missed. User performance data may also include commissions (false positives) calculated, such as a number or percent of occasions in which the user indicated the sequence was present when it was not, or when the symbol in the second display portion that was not supposed to be pressed, e.g., the * on the dashboard, was tapped. User performance data may also include the impact on user performance when the divided attention portion of the test is added to provide a metric of a user's sustained attention and short term memory with and without a divided attention element.

Figure 9:
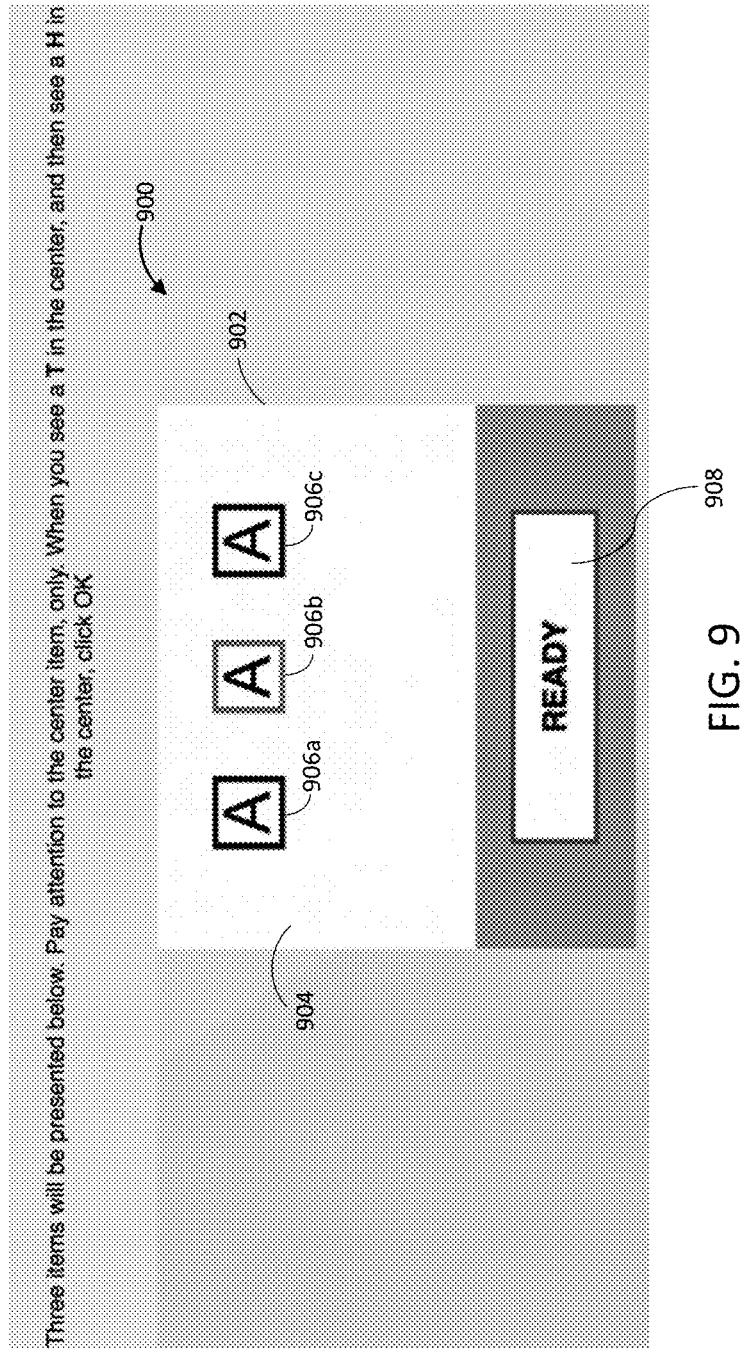
FIG. 9 shows a GUI for one example cognitive test that is designed and configured to test at least sustained attention, short-term memory, and divided attention.

FIG. 9 illustrates another example cognitive test 900 that includes a GUI 902 that may be displayed on a display screen of user interface 112 of user device 102 and includes a display portion 904 that displays a plurality of display elements 906a-906c and a user control element. Cognitive test 900 is an example of one of cognitive tests 302 (FIG. 3). In the illustrated example, display elements 906 display time-varying symbols and user may be instructed to monitor for a particular spatial and/or time-based pattern of symbols and to press user control element 908 when the user sees the target sequence. For example, the user may be instructed to only monitor the center display element 906b and press control element 908 when the center display element displays a time-varying target sequence of a first target symbol followed by a second target symbol. The user may alternately be instructed to monitor for any other variation of time varying or spatial sequences such as a particular sequence of symbols displayed by display elements 906a-c at the same time, such as A-B-C. Test 900 is similar to test 800 and tests sustained attention 420 and short-term memory 416 by requiring the user to remember a particular sequence of symbols and requiring the user to maintain attention as various symbols appear. In some examples, a divided attention element may be added to test 900, such as incorporating a second display element for the user to monitor concurrently with display elements 906a-906c for a separate symbol or pattern.

Figures 10A, 10B:
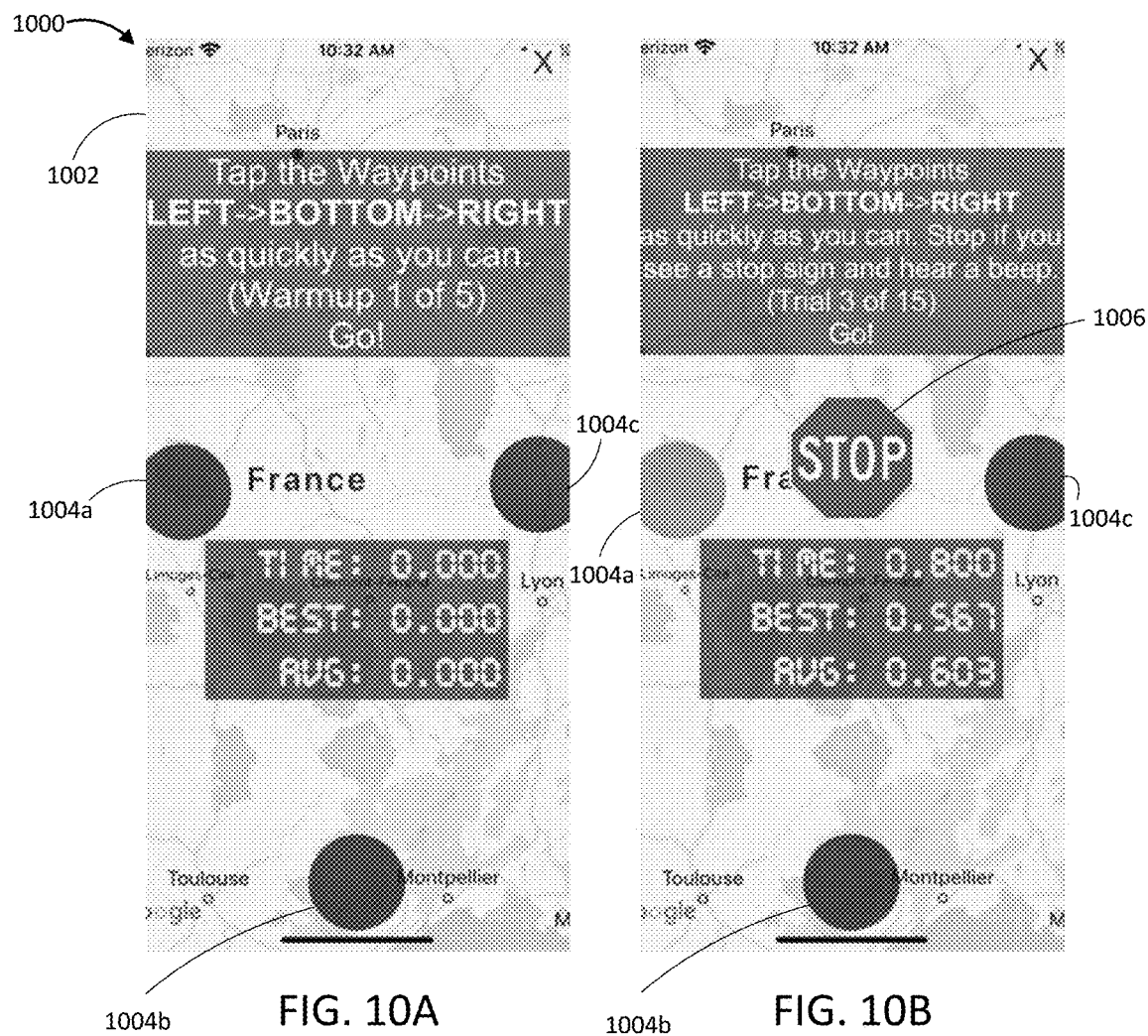
FIGS. 10A and 10B show a GUI for one example cognitive test that is designed and configured to test at least psychomotor control and response inhibition.

FIGS. 10A and 10B illustrate another example cognitive test 1000 that includes a GUI 1002 that may be displayed on a display screen of user interface 112 of user device 102 and includes a display portion that includes a plurality of color-varying touch sensitive control elements, for example, touch sensitive control elements 1004a, 1004b, and 1004c. Cognitive test 1000 is an example of one of cognitive tests 302 (FIG. 3). In the illustrated example, test 1000 includes a first portion of trials where the user is instructed to press the touch sensitive control elements 1004a, 1004b, and 1004c, for example, in a particular sequence, as fast as he or she can, for example, press control element 1004a, then 1004b, then 1004c. The first portion is designed to test psychomotor control 402 by testing the proximity of a user's point of contact to each control element 1004 (for example, how close the location of contact of the user's finger is to the center of each control element), and the speed at which the user can press the sequence of control elements. The first portion of test 1000 is also designed to increase a user's engagement, encouraging the user to gain familiarity and accomplish the sequence as quickly as he or she can. Example test 1000 also includes a second portion of trials where the user is again instructed to press control elements 1004 in the same sequence as the first trial and as fast as possible but also instructed to stop immediately when a stop symbol, such as a stop sign 1006 (FIG. 10B) appears and/or when the user device emits a particular sound, like a beeping noise, instructing the user to stop. The second portion of test 1000 tests response inhibition 410, also referred to as impulse control and psychomotor control 402 in the form of reaction time by testing how quickly the user can stop after he or she has become engaged and is moving as fast as possible. In other examples, other arrangements of control elements 1004 may be used and more or less than three control elements 1004 may be used. In one example instructions for the first portion of trials may include: "Using ONE FINGER, tap A, B and C as they appear from LEFT to RIGHT as quickly as you can!" In one example, all three control elements 1004 appear on the screen and GUI 1002 provides positive feedback when the user successfully makes contact with each control element 1004. For example, control elements 1004 may change color, additional symbols such as stars or confetti may appear, or audible or haptic feedback may be used to gamify test 1000 and engage the user. The second portion of trials may include instructions such as: "Using ONE FINGER, tap A, B, and C from LEFT to RIGHT as quickly as you can with one finger. Stop if you see a STOP sign appear and hear a beep!"

Impairment assessment application 104 and impairment assessment service 124 may be configured to collect and process a variety of user performance data from cognitive test 1000. Non-limiting examples of user performance data include reaction time, speed, and touch accuracy during the first portion of trials, accuracy of performance on the second portion of stop trials, for example the number of control elements pressed after the stop signal an change in reaction time between the first and second portion of trials.

Figure 11:
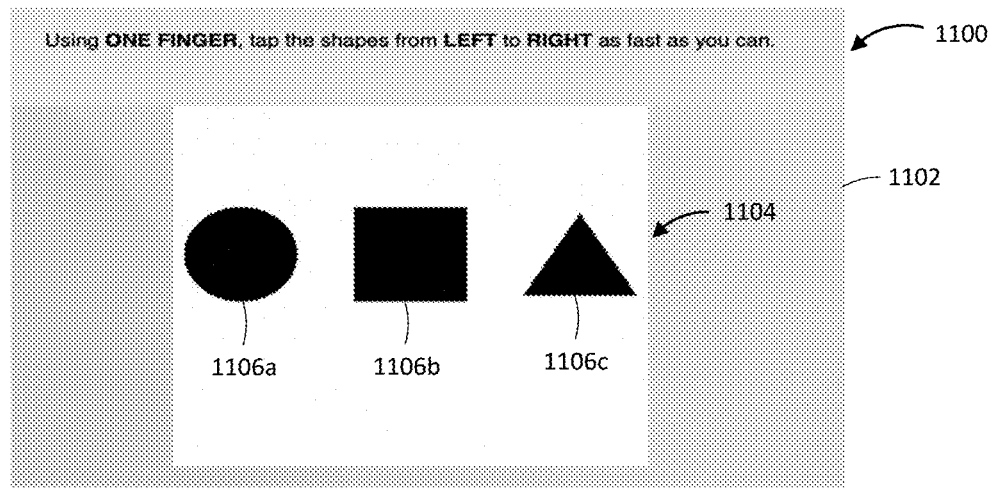
FIG. 11 shows a GUI for one example cognitive test that is designed and configured to test at least psychomotor control and response inhibition.

FIG. 11 illustrates another example cognitive test 1100 that includes a GUI 1102 that may be displayed on a display screen of user interface 112 of user device 102 and includes a display portion 1104 that includes a plurality of color-varying touch sensitive control elements, for example, touch sensitive control elements 1106a, 1106b, and 1106c. Cognitive test 1100 is an example of one of cognitive tests 302 (FIG. 3). In the illustrated example, test 1100 has a similar configuration to test 1000 (FIGS. 10A and 10B) and includes a first portion of trials where the user is instructed to press the touch sensitive control elements 1106a, 1106b, and 1106c, for example, in a particular sequence, as fast as he or she can, for example, press control element 1106a, then 1106b, then 1106c. The first portion is designed to test psychomotor control 402 by testing the proximity of a user's point of contact to each control element 1106 (for example, how close the location of contact of the user's finger is to the center of each control element), and the speed at which the user can press the sequence of control elements. The first portion of test 1100 is also designed to increase a user's engagement, encouraging the user to gain familiarity and accomplish the sequence as quickly as he or she can. Example test 1100 also includes a second portion of trials where the user is again instructed to press control elements 1106 in the same sequence as the first trial and as fast as possible but also instructed to stop immediately when a stop symbol, such as a stop sign (not illustrated) appears and/or when the user device emits a particular sound, like a beeping noise, instructing the user to stop. The second portion of test 1100 tests response inhibition 410, also referred to as impulse control and psychomotor control 402 in the form of reaction time by testing how quickly the user can stop after he or she has become engaged and is moving as fast as possible. In other examples, other arrangements of control elements 1106 may be used and more or less than three control elements 1106 may be used. In one example instructions for the first portion of trials may include: "Using ONE FINGER, tap the three shapes from LEFT to RIGHT as quickly as you can!" In one example, all three control elements 1106 appear on the screen and GUI 1102 provides positive feedback when the user successfully makes contact with each control element 1106. For example, control elements 1106 may change color, additional symbols such as stars or confetti may appear, or audible or haptic feedback may be used to gamify test 1100 and engage the user. The second portion of trials may include instructions such as: "Using ONE FINGER, tap the three shapes from LEFT to RIGHT as quickly as you can with one finger. Stop if you see a STOP sign appear and hear a beep!"

Impairment assessment application 104 and impairment assessment service 124 may be configured to collect and process a variety of user performance data from cognitive test 1100. Non-limiting examples of user performance data include reaction time, speed, and touch accuracy during the first portion of trials, accuracy of performance on the second portion of stop trials, for example the number of control elements pressed after the stop signal an change in reaction time between the first and second portion of trials.

Figure 12:
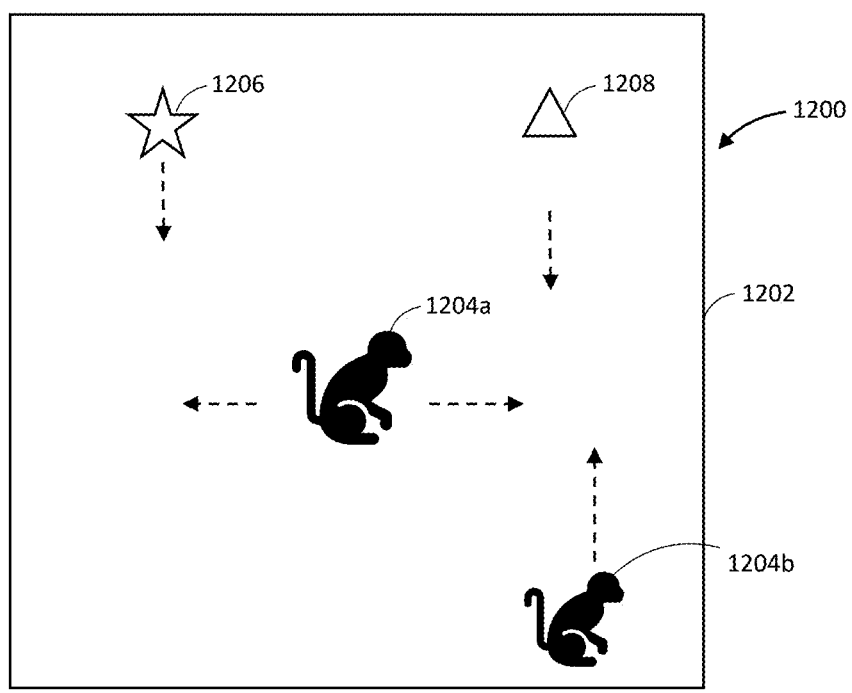
FIG. 12 shows a GUI for one example cognitive test that is designed and configured to test at least psychomotor control and divided attention.
Figure 12:
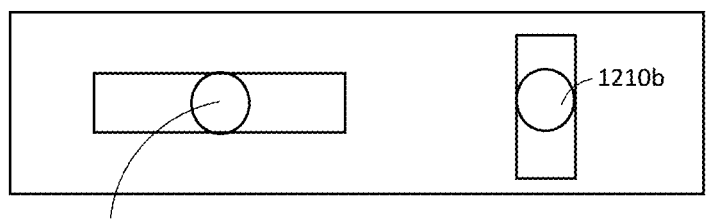

FIG. 12 illustrates another example cognitive test 1200 that includes a GUI 1202 that may be displayed on a display screen of user interface 112 of user device 102 and includes a display portion that includes first and second game characters 1204a and 1204b (in the illustrated example two monkeys) a plurality of moving target objects 1206 and a plurality of moving avoidance objects 1208. GUI also includes user control elements 1210a and 1210b for controlling a position of game characters 1204. In one example, both control elements 1210 are soft control elements displayed graphically on a touch sensitive display and are displayed as slide bars for linear control. In one example control element 1210 is a lateral control element and controls character 1204a in a side to side direction and control element 1210b is a vertical control element and controls character 1204b in a vertical direction.

In one example, character 1204a is shown climbing a tree (not illustrated) by displaying a tree in the background that is moving down relative to the character and the user is instructed to pick up food (target objects 1206) along the length of the tree trunk as the character climbs, but avoid objects falling from the top of the tree (avoidance objects 1208). The background advances at a particular rate forcing the character to climb, the rate can be increased or varied during the course of a trial and/or in subsequent trials. The user is instructed to guide character 1204a (for entertainment the character may be described as "momma monkey") using lateral control element 1210a to align the character with fruits (target objects 1206) as they appear on the trunk and avoid objects dropping at random along the tree trunk (avoidance objects 1208). In one example, as the test progresses, fruits (target objects 1206) and falling objects (avoidance objects 1208) appear more frequently, making the game more difficult.

In a second iteration of test 1200 (trial 2) vertical control element 1210b is displayed along with second game character 1204*b* (which for entertainment and user engagement may be described as "baby monkey"). As with the first trial, lateral control element 1210*a* causes character 1204*a* to move left or right, and in the second trial, character 1204*b* follows in unison. To assess divided attention, second character 1204*b* does not automatically advance up the tree with character 1204*a* and the user is required to divide his or her attention by monitoring a position of second character 1204*b* and use vertical control element 1210*b* to move character 1204*b* up as it approaches the bottom of the screen. If second character 1204*b* touches the bottom of the screen, he falls off, and in some examples, a user is prevented from advancing second character 1204*b* vertically above first character 1204*a* as it climbs up the trunk.

Game 1200 is designed to test psychomotor control 402 by assessing the user's ability to use control elements 1210 to effectively control characters 1204 in the manner instructed and in the second trial, divided attention 418 by assessing the user's ability to simultaneously control both characters 1204*a* and 1204*b*. Impairment assessment application 104 and impairment assessment service 124 may be configured to collect and process a variety of user performance data from cognitive test 1200. Non-limiting examples of user performance data include opportunity errors in the form of proportion of total target objects 1206 missed, time-to-failure, for example, the duration of time until an avoidance object 1208 hits character 1204*a*, a measure of how the opportunity error and time to failure changes when the divided attention element is introduced in the second trial, and the time to failure measured by the duration of time until an avoidance object 1208 hits character 1204*a* or second character 1204*b* hits the bottom of the screen.

Figure 13A:
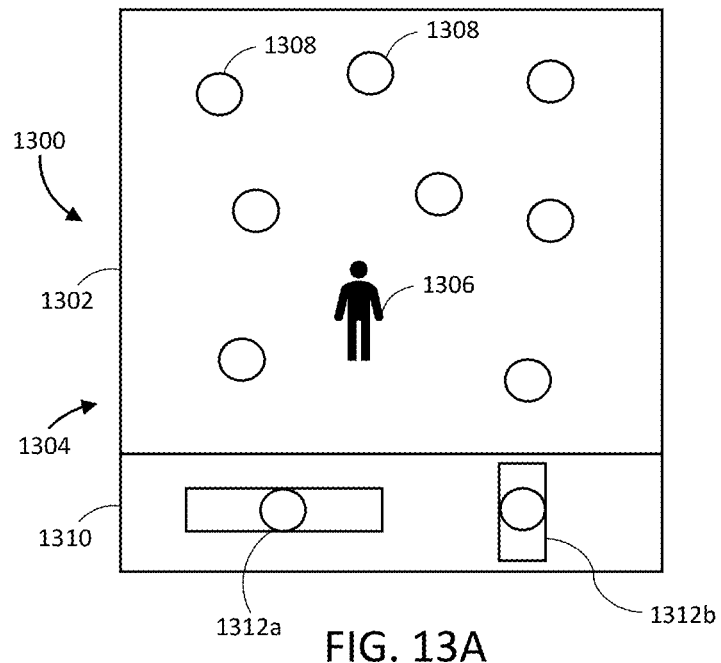
FIGS. 13A-13D show a GUI for one example cognitive test that is designed and configured to test at least psychomotor control, short term memory, working memory, and spatial reasoning.
Figure 13B:
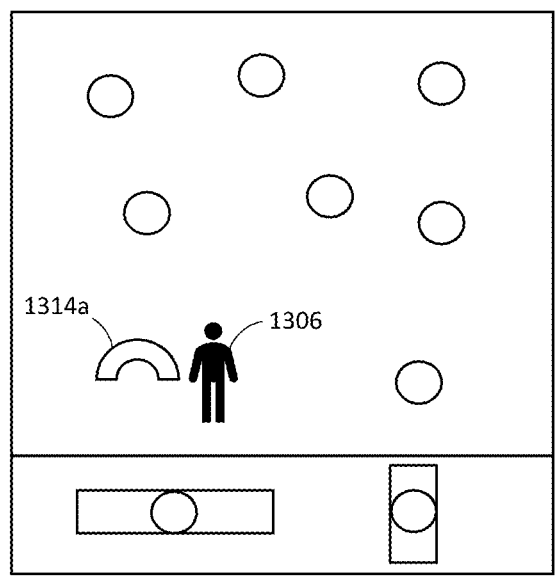
Figure 13C:
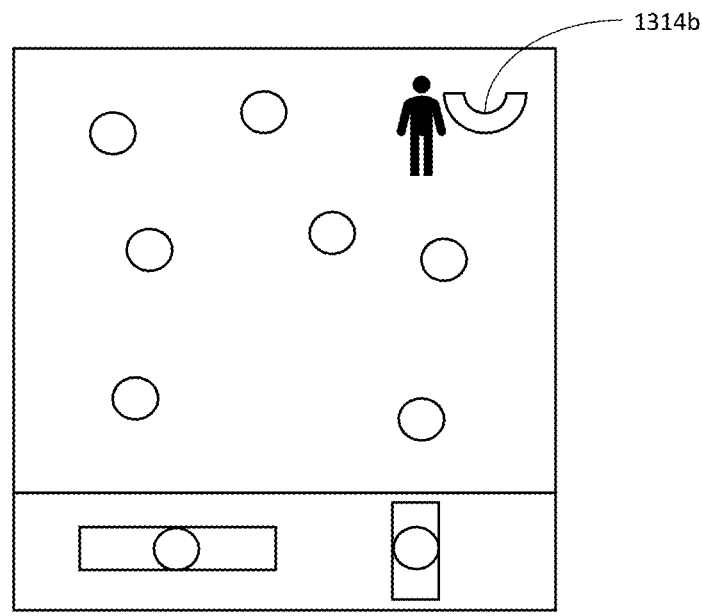
Figure 13D:
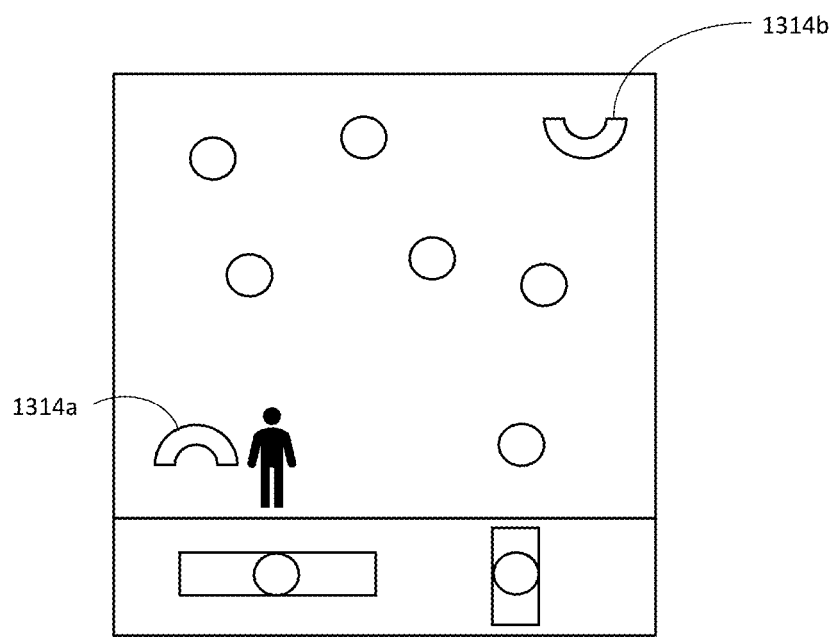

FIGS. 13A-13D illustrate another example cognitive test 1300 that includes a GUI 1302 that may be displayed on a display screen of user interface 112 of user device 102 and includes a display portion 1304 that displays game elements including a character 1306 and a plurality of objects 1308 (only two of which are labeled in FIG. 13A). GUI 1302 also includes a control element portion 1310 that includes user control elements 1312*a* and 1312*b* for controlling a position of character 1306 on display portion 1304. Cognitive test 1300 is an example of one of cognitive tests 302 (FIG. 3). In the illustrated example, test 1300 is a memory game where a user is instructed to move the character 1306 to any of the objects 1308 to reveal a hidden symbol 1314*a* (FIG. 13B). The user is instructed to find matching symbols by moving the character to each of the objects 1308.

Cognitive test 1300 includes instructions to display instructions on GUI 1302 that instruct the user to move character 1306 around the screen to collect whole shapes formed by the combination of two or more matching symbols 1314 (shown conceptually as two halves 1314*a* (FIG. 13B) and 1314*b* (FIG. 13C) of a circular object). The user moves the character 1306 away from one object 1308, thereby hiding symbol 1314 again and looks for the counterpart or matching symbol 1314. When character 1306 touches each symbol pair (1314*a* and 1314*b*) sequentially (without touching an intervening object/symbol) and within a maximum allotted time period, the user collects the completed whole shape and earns points. Because the symbol 1314 is hidden when the character 1306 is moved away from it, the user is required to remember which objects 1308 contain each symbol portion (e.g. where the last matching symbol was last encountered). This is conceptually illustrated in FIGS. 13A-13D, where, in FIG. 13B, the user uncovers symbol 1314*a*, in FIG. 13C the character is moved away from the object covering symbol 1314*a* and it is rehidden but the user has uncovered the matching symbol 1314*b* under another object, and then in FIG. 13D the user recalls where symbol 1314*a* is hidden, moves character 1306 back to that location, and is awarded the matching pair. Test 1300 can be implemented in a variety of forms, adding gamification elements to increase user engagement. For non-limiting example, character 1306 can be displayed as a fantasy character, such as a troll, objects 1308 can be displayed as boulders, and symbols can be displayed as portions of colorful gens the troll is seeking to collect.

In the illustrated example, there are multiple objects 1308 in GUI 1302 such that the user will find other half-symbols (e.g. two halves of a star (not illustrated). The character advances to the next object-field screen when all symbol-pairs are collected; there may be any number of symbol pairs, for example, as many as five pairs per object field and in some examples with increased difficulty, as many as 25 objects 1308 (only some of which contain symbols 1314). In one example, test 1300 includes instructions to vary a speed of movement of the character 1306 to decrease the characters speed (moves more slowly across the screen) so that a user will be required to retain the symbol locations in his or her memory for a longer period of time and to increase the likelihood the user will be required to keep track of multiple symbol locations at the same time. In some examples, test 1300 is configured to randomly assign the location of symbol pairs 1314 for each trial and in some examples, test 1300 is configured to automatically display symbols from two or more different pairs as the user uncovers the first two or more objects 1308 to ensure the user is required to simultaneously maintain the location of multiple symbol pairs in his or her memory.

Test 1300 is configured to test short term memory 416 because the user is required to retain the location of previously uncovered symbols 1314 and working memory 414 because the user is required to temporarily store and manipulate information in short term memory (symbols) by forming matching pairs. Test 1300 also tests psychomotor control 402, spatial reasoning 412 in the form of spatial navigation (required to navigate the character 1306 around the screen), and sustained attention 420.

Impairment assessment application 104 and impairment assessment service 124 may be configured to collect and process a variety of user performance data from cognitive test 1000. Non-limiting examples of user performance data include time-to-complete an object-symbol screen (when all symbol pairs are identified and collected), for example, the duration of time it takes for the user to complete the task proportionate to the amount of time allotted and/or the number of symbol pairs. Performance data may also include commission errors, such as the touching of a previously encountered object 1308 that is misidentified as a symbol counterpart. In one example, the test ends after a few screens, or after a set amount of time elapses.

Figure 14:
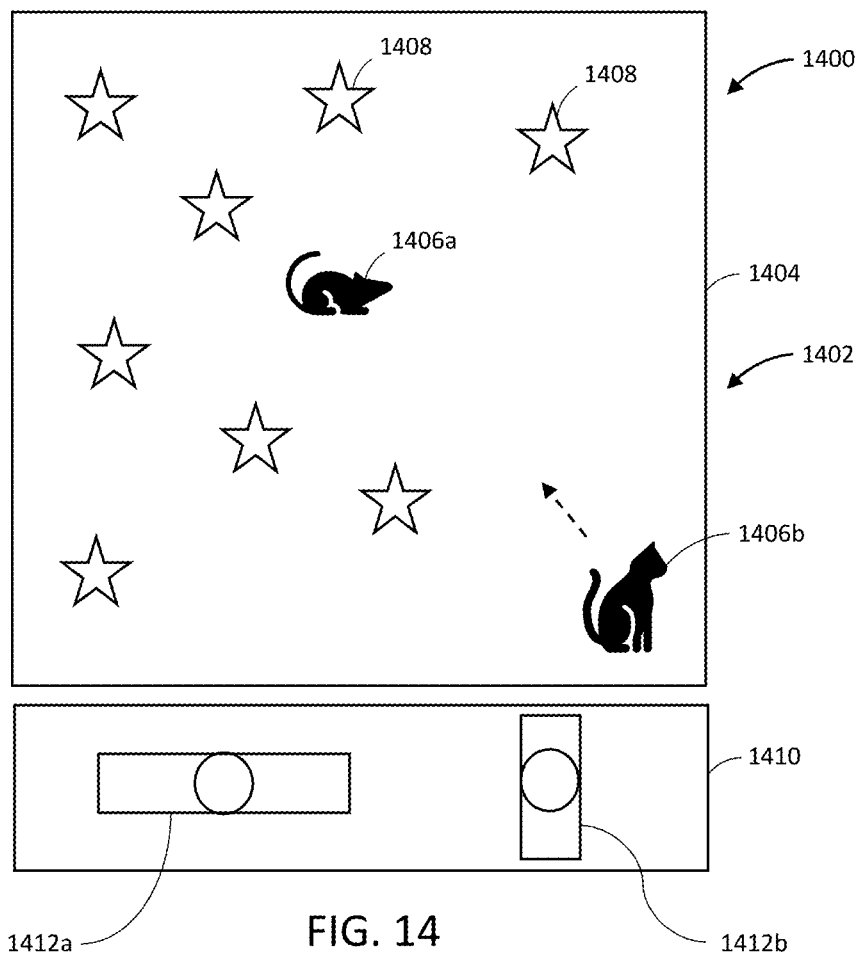
FIG. 14 shows a GUI for one example cognitive test that is designed and configured to test at least psychomotor control and risk taking.

FIG. 14 illustrates another example cognitive test 1400 that includes a GUI 1402 that may be displayed on a display screen of user interface 112 of user device 102 and includes a display portion 1404 that displays game elements including a first character 1406*a*, a second character 1406*b* and a plurality of objects 1408 (only two of which are labeled). GUI 1402 also includes a control element portion 1410 that includes user control elements 1412*a* and 1412*b* for controlling a position of character 1406*a* on display portion 1404. Cognitive test 1400 is an example of one of cognitive tests 302 (FIG. 3). In the illustrated example, test 1400 is a risk sensitivity and probability assessment in the form of a game that tests a user's risk tolerance, in the illustrated example, by presenting a foraging task in which a character 1406*a* (in the illustrated example, a mouse, or any other animal) forages for objects 1408 (which may be illustrated as a food source such as cheese) in the midst of a predator (character 1406*b*, e.g., a cat). The longer character 1406*a* stays amongst objects 1408 increase its consumption of the objects but also increases the probability it will get eaten by character 1406*b*. In one example, user control elements 1412 can be used to move character 1406*a* around display portion 1404 to collect objects 1408 while character 1406*b* (the cat) gradually approaches. The rate at which character 1406*b* approaches and the direction it moves may vary, adding randomness that makes it difficult for the user to predict when the cat will attack. The user may be instructed to press a user control element to "escape" to safely exit the game with the objects that have been collected. The longer a user waits to press the escape button and the closer the user allows the cat to get to the mouse the higher the user's apparent risk-tolerance.

In another example, cognitive testing module 202 may include additional or alternate risk sensitivity and probability assessment tests in the form of a game that tests a user's risk tolerance, for example, a gambling game (not illustrated). In one example, a gambling game may be configured to present a modified version of blackjack in which the goal is to approach a target number, e.g., 10, without busting. In one example, the dealer always has a 7 showing, and the user is only playing against the dealer, and the dealer takes the last hit. In one example, the gambler has a card that varies between 4-6, and the user is instructed to press a "hit" or "stay" user control element, e.g., displayed on GUI. In one example, the gambling cognitive test includes instructions for varying the cards dealt to the gambler but to increase the likelihood of getting a higher card (e.g. >5) with each successive hit, thereby making it more likely with each successive hit for the user to "bust" and lose the game. In one example, each hand earns the user (player of the game) a certain amount of money or points and the player gets to keep playing until they go broke. The example gambling cognitive tests, therefore, present the risk of going over a target number, e.g., 10 and the risk that the dealer will beat the user, and the user is required to weigh each risk to make the appropriate decision. The more hits a user takes and the more often he or she busts the higher the user's apparent risk-tolerance. In one example, user performance data may include a number of "hits" the user elects to take relative to the sum of the value of the cards the user has when he or she takes the hit. For example, if the user elects to take a hit at 9 (one point away from the limit) this represents a greater degree of risk taking than if the user takes a hit at 4 or 6. In other examples, user performance data may be based on other calculations, for example, relating to the decision to hit or not hit relative to, e.g., prior cards presented, a dealer's current hand, etc.

In one example, cognitive test 1400 and/or another risk tolerance test, such as a gambling game may be included in screening test module 304 and/or substance identification test module 306 because different substances have differing impacts on an individual's risk tolerance. For example, alcohol and benzodiazepines may have a higher likelihood to increase a user's risk taking than cannabis. Accordingly, cognitive testing module 202 may be designed and configured to determine one or more of a selection of cognitive tests 302 and a sequence of the tests according to how a user performs when playing cognitive test 1400. For example if user performance data from cognitive test 1400 indicates an increased risk tolerance, that can be used as an indication that the user is more likely suffering from a cognitive impairment caused by a first group of substances, such as alcohol and benzodiazepines, etc.) and less likely the user is suffering from a cognitive impairment caused by a second group of substances that may include cannabis.

Figure 15:
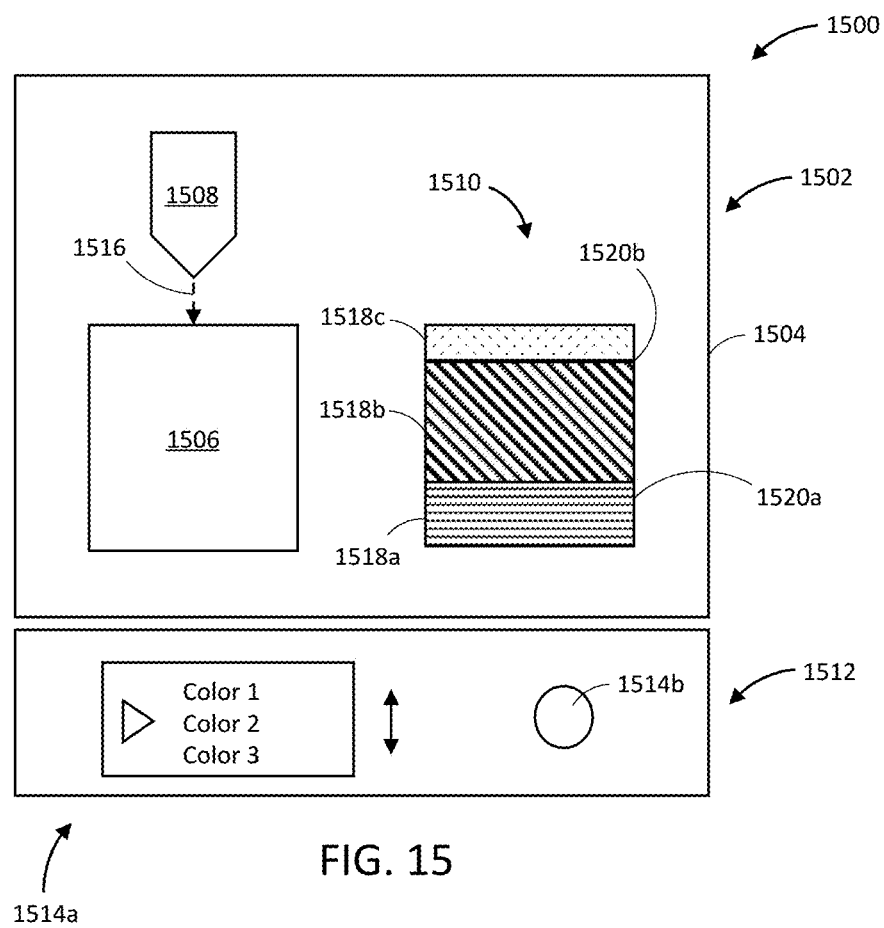
FIG. 15 shows a GUI for one example cognitive test that is designed and configured to test at least psychomotor control and creativity and/or spatial reasoning.

FIG. 15 illustrates another example cognitive test 1500 that includes a GUI 1502 that may be displayed on a display screen of user interface 112 of user device 102 and includes a display portion 1504 that displays game elements including a container 1506 a dispenser 1508 and a target pattern 1510. GUI 1502 also includes a control element portion 1512 that includes user control elements 1514*a* and 1514*b* for creating a pattern in container 1506. Cognitive test 1500 is an example of one of cognitive tests 302 (FIG. 3). In the illustrated example, test 1500 is designed and configured to test a user's spatial reasoning 412 (FIG. 4) by testing the user's ability to create a pattern in container 1506 that matches the target pattern 1510. In the illustrated example, user control element 1514*a* allows the user to select a color of the material 1516 emitted from dispenser 1508 and user control element 1514*b* stops and starts the material from flowing from the dispenser. In the illustrated example, GUI is configured to display material 1516 as having a fluid characteristic, such as a liquid or sand and in some examples, includes instructions for varying a rate at which the material collects in container 1506, for example, a slower rate for an easier test that is primarily testing spatial reasoning and a faster or variable rate for also testing psychomotor control (402) such as reaction time. In some examples, the complexity can be increased by adding another user control element 1514 to control a lateral position of dispenser 1508 relative to container 1506 and material 1516 can be displayed as having a more viscous or solid characteristic such that the interface 1520 between layers is not a horizontal line. Target pattern 1510 may similarly have a more complex shape where the interface 1520 between layers 1518 is not a horizontal line but an angled line and/or more than one color may be directly adjacent and located at the same height in the container. In the more complex example, the user is instructed to move dispenser 1508 left and right to match not only the color but also the shape of the target pattern 1510.

By stopping and starting the flow of the material 1516 with control element 1514*b* and controlling the color with control element 1514*a* the user can try to create a pattern of colors in container 1506 that matches target pattern 1510. Although three layers 1518 of colors are shown, any number of colors may be used. In other examples, cognitive tests 302 may include any other spatial reasoning tests known in the art as an alternative or in addition to example test 1500, such as tests that instruct a user to select one of a plurality of three-dimensional or two-dimensional shapes that matches a target two or three dimensional shape, among others, as is known in the art of spatial reasoning tests.

Impairment assessment application 104 and impairment assessment service 124 may be configured to collect and process a variety of user performance data from cognitive test 1500. Non-limiting examples of user performance data include speed of reproduction, for example, by the time it takes of the user to completely fill the container 1506 with the falling material 1516 relative to the amount of time allotted and accuracy of the reproduction measured, for example, by comparing the proportion of each color to the proportions of each color in the target, for example, calculated as a percentage based of the proportion of pixels that mismatch the pixelated target.

In another example, a modified version of test 1500 may be used to test a user's creativity 408 (FIG. 4). In the modified version, the target pattern 1510 is omitted and the user is instructed to create any pattern he or she desires in container 1506. User performance data from the creativity task may include a creative intelligence metric in the form of a design complexity metric, for example, a number of colors that were used; the variation in thickness of each color layer; in examples that include side-to-side control of dispenser 1508, variation in thickness of each color layer across the width of the container; and the amount of time the user took to complete the task (longer time indicating the user was more engaged and enjoyed the creative task). The creativity cognitive test program may also be configured to present the user with a questionnaire to measure task enjoyment, such as 7-point Likert or visual analog scale, at the end of the task to ask the user if he or she enjoyed playing the game.

In one example, a creativity test may be included in screening test module 304 and/or substance identification test module 306 because different substances have differing impacts on an individual's desire to perform a creativity task. For example, cannabis may cause a user to enjoy a creativity task more than other substances, such as alcohol. Accordingly, cognitive testing module 202 may be designed and configured to determine one or more of a selection of cognitive tests 302 and a sequence of the tests according to how a user performs when playing cognitive test 1400. For example if user performance data from a creativity cognitive test indicates an increased creative intelligence and/or user enjoyment, that can be used as an indication that the user is more likely suffering from a cognitive impairment caused by a first group of substances, such as a group that may include cannabis and less likely the user is suffering from a cognitive impairment caused by a second group of substances.

In another example, cognitive testing module 202 may include a cognitive test (not illustrated) configured with a GUI designed to be displayed on user interface 112 that is configured to test response inhibition 410 and psychomotor control 402 including reaction time and psychomotor vigilance, by requiring the user to respond as quickly as possible to a target presented on screen at random times and locations. In one example, the test is presented as a game, and the user is instructed to tap on user control elements in the display, such as various objects, such as symbols, letters, or numbers, e.g., an X, as they appear at random intervals in random locations around the screen. Tapping the object causes it to disappear. In one example, the rate of object appearance increases with extended play. The user may also be instructed to avoid touching other objects (e.g. "#"). In some examples, the "no touch" objects disappear soon after they appear whether or not they're touched.

Impairment assessment application 104 and impairment assessment service 124 may be configured to collect and process a variety of user performance data from the cognitive test. Non-limiting examples of user performance data include omissions are the proportion of target objects missed "X" versus the total number of targets presented and commissions, for example, the proportion of distractor objects "#" touched out of the total number of distractor objects presented; reaction time, for example, the average time interval between when the target object X is presented and it is touched; and/or touch accuracy, such as how close the user's finger was to the center of each object that was touched.

Example Questionnaires

Figure 16A:
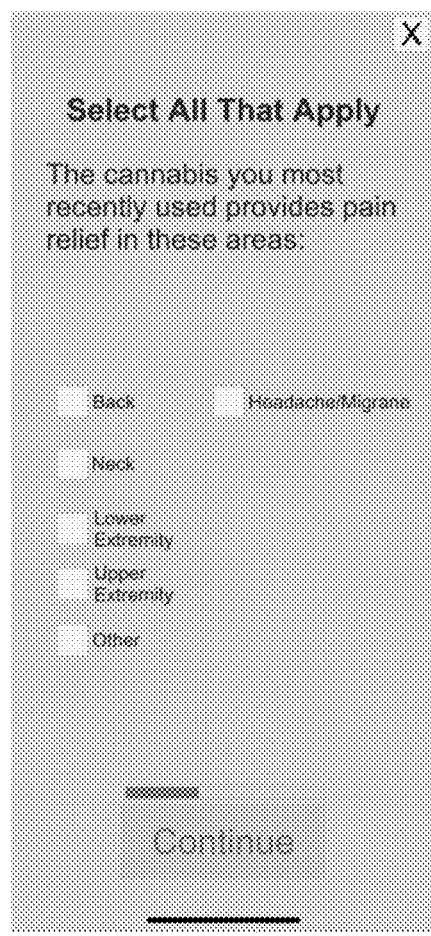
Figures 16B, 16C:
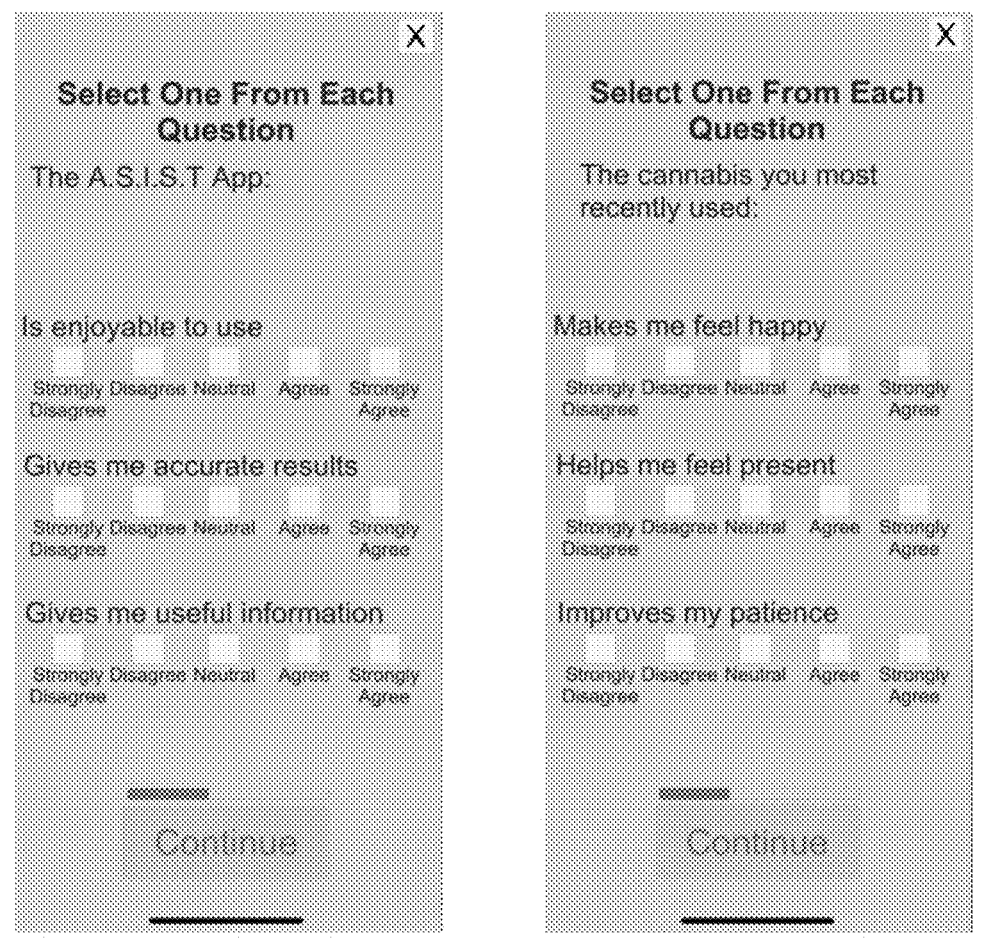
Figures 16D, 16E:
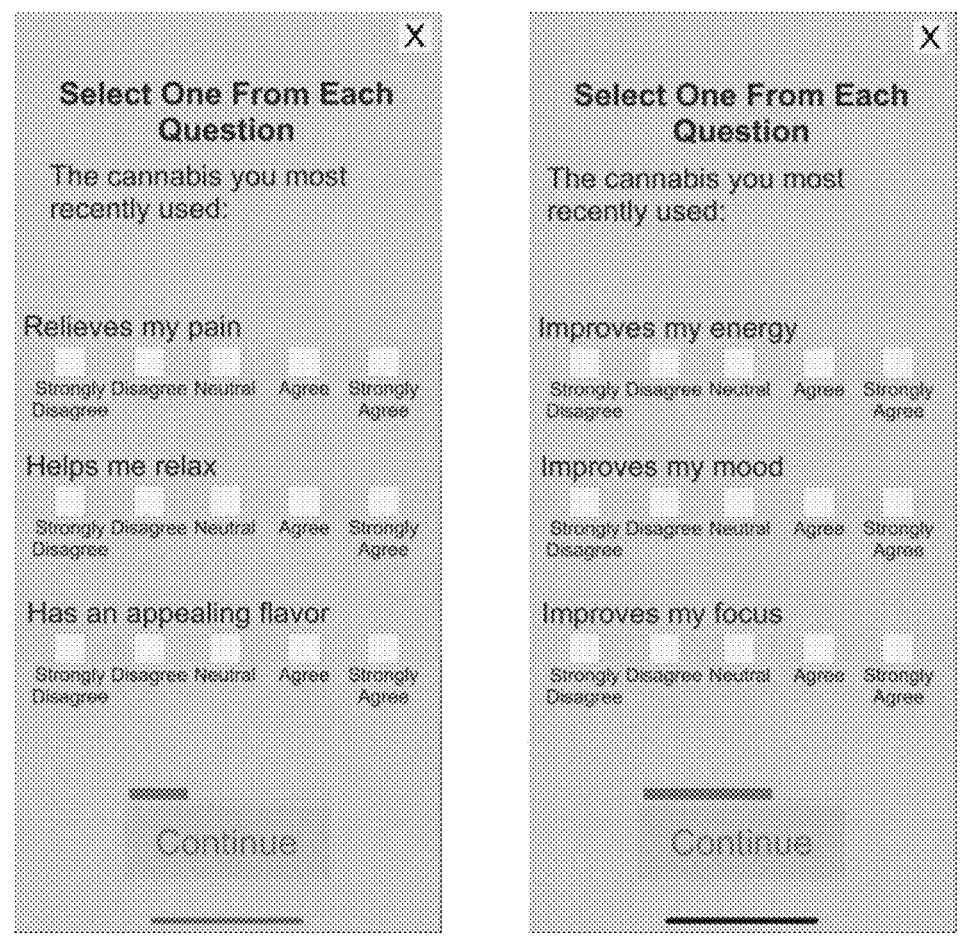
Figures 16F, 16G:
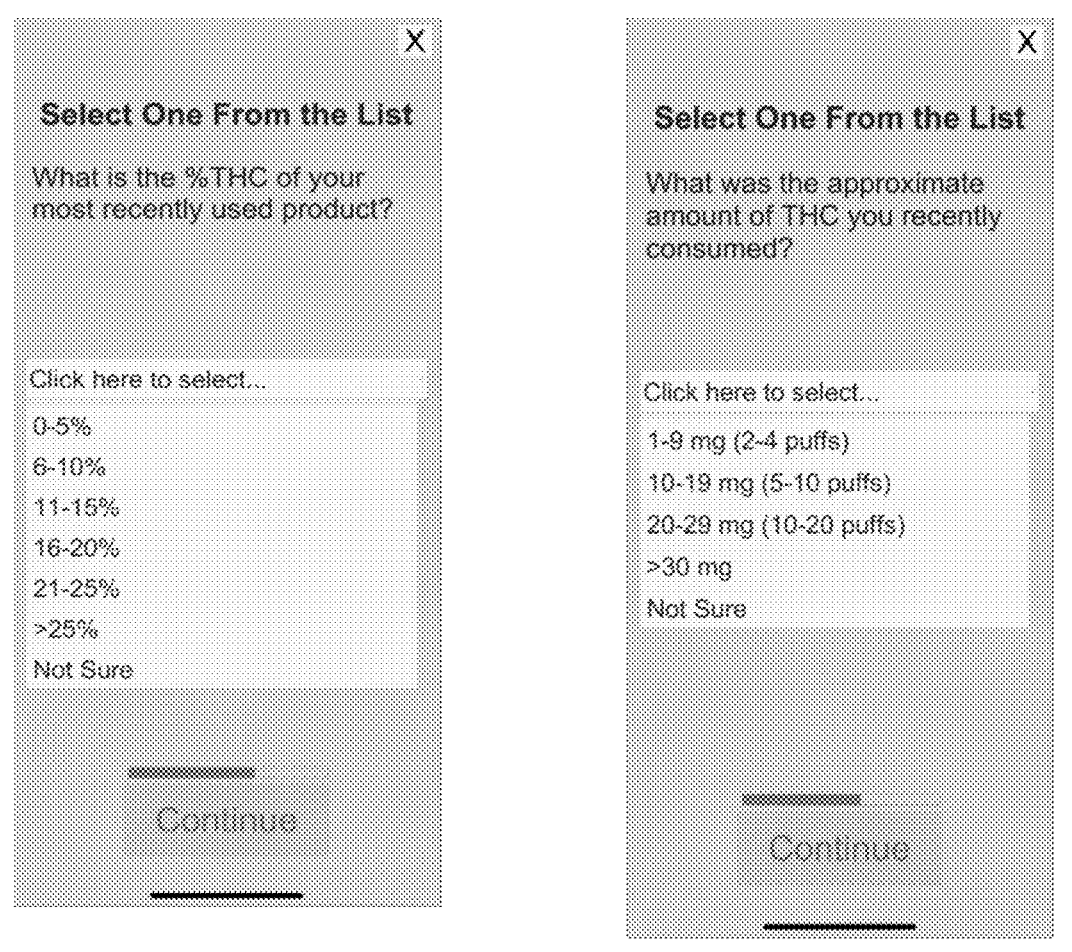
Figures 16H, 16I:
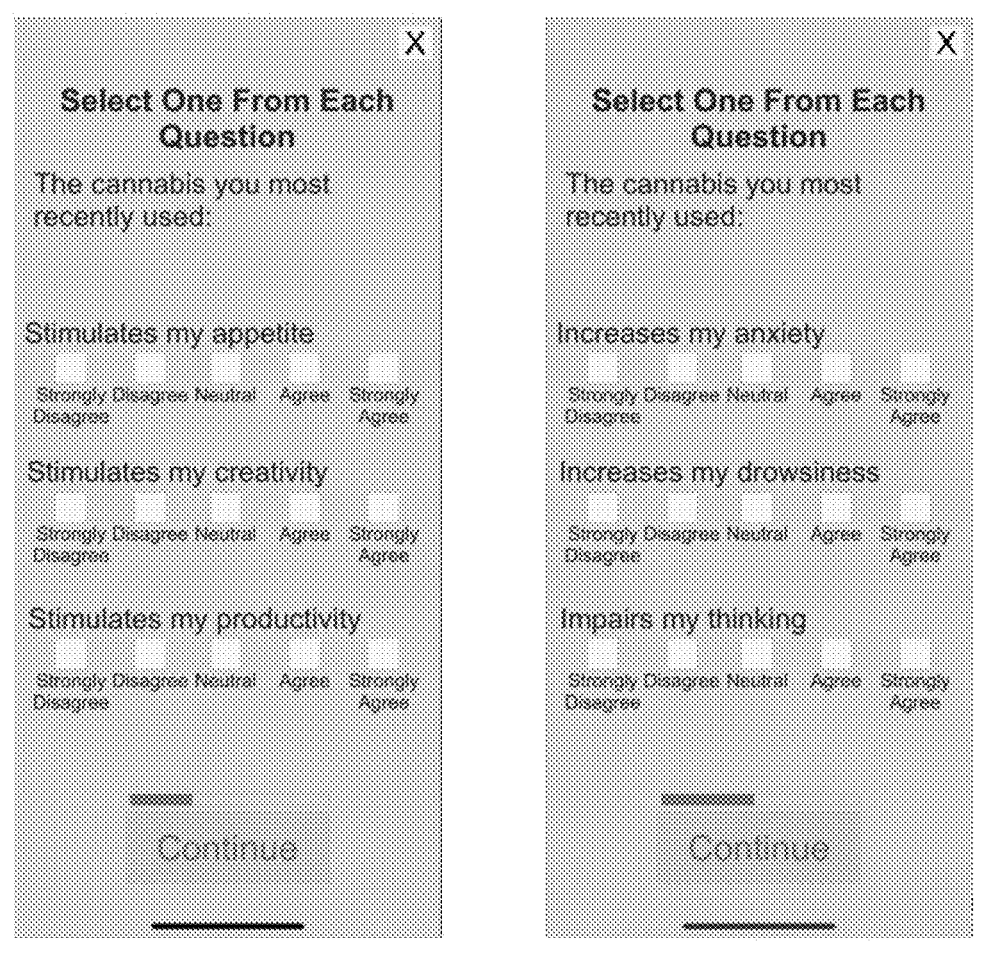
Figures 16J, 16K:
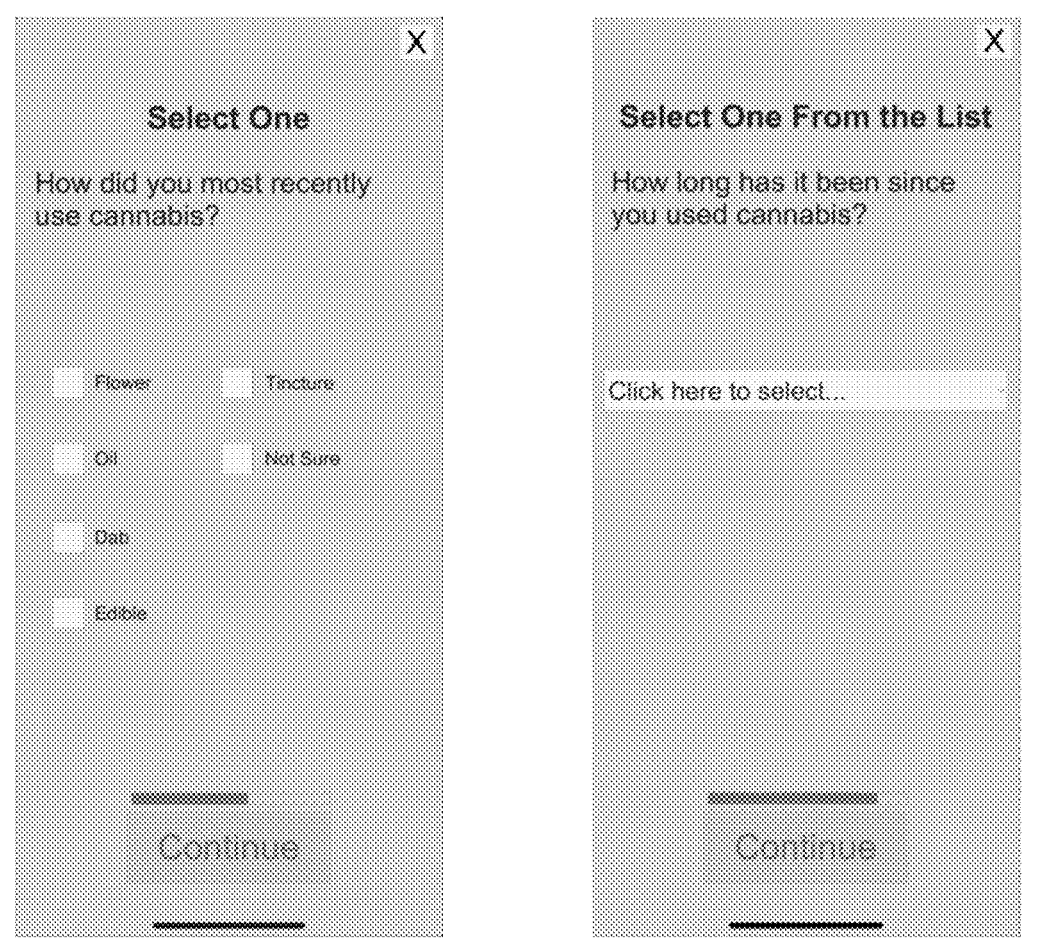
Figure 16L:
Figure 16M:
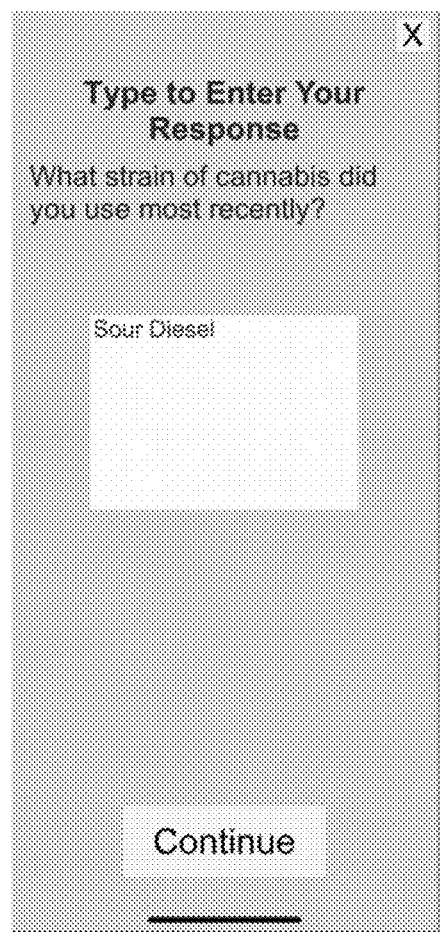

FIGS. 16A-16M are example questionnaires that questionnaire module 204 may be configured to display on user interface 112 to collect questionnaire data 132 that may be used by system 100 in combination with cognitive test data 132 and physiological test data 136 for any of a variety of purposes, such as for determining a personalized or standard dosage amount and/or a standard impairing dose threshold for a particular substance. Questionnaire data 132 may also be used for creating training data for one or more machine learning algorithms utilized by impairment assessment service 124 by classifying cognitive test data 132 and physiological test data 136 according to type and amount of substance. Questionnaires such as the example questionnaires illustrated in FIGS. 16A-16M may be presented by impairment assessment application 104 in sequence with, before, or after the presentation of cognitive tests 302. Questionnaire module is configured to instruct the user input subjective information about their current experience, including his or her experience related to the gaming experience and/or the substance he or she has ingested. Subjective information collected by questionnaire module 204 can complement cognitive test data 132 and physiological data 136. The example questionnaires illustrated in FIGS. 16A-16M collect questionnaire data including impact on pain relief, subjective impact of a substance on a user's cognitive state, including happiness, concentration, patience, etc. (FIGS. 16A, 16C-E, 16H, 16I); general user experience with the impairment assessment application (FIG. 16B); and characteristics of ingested substance, such as potency, dosage, method of ingestion, type, etc. (FIGS. 16F, 16J, 16L, 16M, and the user's history of substance use, e.g. FIG. 19K.

Physiological Testing Module

In some implementations, impairment assessment software applications made in accordance with the present disclosure may include physiological testing module 206 that includes instructions for collecting physiological sensor data of a user's physiology, including but not limited to information on and measurement of a user's pupils, head movements, heart rate, heart rate variability, respiratory rate, and blood pressure which can be collected and processed to determine a likelihood of impairment.

Non-limiting examples of physiological data 136 include ocular-motor and pupil-reflex features, such as dilation, rebound dilation, tracking (each eye independently and in coordination), convergence, object tracking and nystagmus, and heart rate, blood pressure, and respiratory rate data. In one example, physiological testing module 206 may be configured, during the course of gameplay, to control camera 106 and light source 110 to assess a user's pupils as they move in relation to one another, and to assess the amount of reflected light from the user's retinas in order to evaluate pupil size. The eye assessments may be collected with varied direct and/or ambient lighting conditions to ascertain physiological data such as pupillary reflex. Physiological testing module 206 may also include instructions for comparing any one or more types of physiological data disclosed herein to previously obtained data from the same user to assess changes relative to the previously-obtained data. For example, images of a user's face indicating bloodshot eyes, droopy eyelids, saccadic eye movement or nystagmus may be compared to previously obtained images, for example, images stored in physiological data 136 of database 130, which may include a driver's license or employee identification card photograph.

Non-limiting examples of physiological data include immediate and sustained convergence, which are ocular-motor responses that are determined by the pupils' relative position to one another; pupil dilation in response to direct, sustained light versus ambient light, which is an indication of drug-related impairment; saccadic eye movement tracking; and nystagmus.

In some examples, physiological testing module 206 is configured with instructions for one or more tests that include GUIs configured to be displayed on user interface 112. One example of a physiological test may include a GUI configured to display an object (not illustrated) in the center of a display screen of user device 102 and instructions that include "Please stare at the dot in the center of the screen." Physiological testing module 206 may be configured to capture images of at least one of the user's eyes and one or more machine vision algorithms for processing and analyzing the captured images. In some examples, physiological testing module 206 may be configured to control light source 110 to emit low ambient light, thereby causing the user's pupils to be dilated; emit direct bright light, thereby causing the pupils to constrict; and emit sustained bright light, captured images of the eyes may be processed by machine vision algorithms to determine whether the pupils remain constricted or if they prematurely return to being dilated. Physiological testing module 206 may also include machine vision algorithms to assess whether sclera is red or bloodshot, the presence of tearing, and ptosis (whether one or both eyelids are droopy).

In another example, a physiological test may include a GUI configured to test eye convergence by displaying an object (not illustrated) in the center of a display screen of user device 102 that moves fluidly around a screen, and then centers on the screen and grows rapidly larger (as if approaching the user). The GUI may display instructions that include "Please stare at the dot in the center of the screen." Physiological testing module 206 may be configured to capture images of the user's eyes with camera 106 and process the images to track the user's pupils and/or irises while the user follows the cursor as it moves fluidly around the screen and then centers on the screen and grows rapidly larger. GUI may also be configured to display an object with a three-dimensional appearance to further assess eye convergence. Physiological testing module 206 may be configured to determine whether the user's pupils can smoothly track the moving object or if there is erratic (saccadic) movement and whether the user's eyes are able to converge on the center but not stay converged for more than 2-3 seconds.

In some examples, physiological testing module 206 may be configured to capture images of a user's face and eyes while the user is taking one or more of cognitive tests 302 and process the images to provide a physiological assessment concurrently with the cognitive assessment performed by cognitive testing module. In some examples, one or more of cognitive tests are designed to elicit a physiological response during the execution of the cognitive test. For example, during performance of one or more of the cognitive tests 302, physiological testing module may be configured to vary a brightness of a display of the user interface 112 and/or control light source 110 to increase or decrease a brightness of emitted light in order to evoke a pupillary response to assess pupil dilation. Physiological testing module may also be configured to capture and process images of a user's eyes during the performance of a cognitive test 302 that involves moving objects, such as one or more of cognitive tests 600 (FIGS. 6A-6D), 800 (FIGS. 8A-8D, and 1200 (FIG. 12) to determine the presence of saccadic movement and eye convergence. In one example, a cognitive test 302 may be configured to simultaneously test psychomotor control 402 including reaction time and psychomotor vigilance as well as physiological data including saccadic movement and eye convergence by requiring the user to respond as quickly as possible to a target presented on screen at random times and locations, the location of the target designed to test for eye convergence. In one example, the test is presented as a game, and the user is instructed to tap on user control elements in the display, such as various objects, such as symbols, letters, or numbers, e.g., an X, as they appear at random intervals in random locations around the screen.

Figures 17, 18:
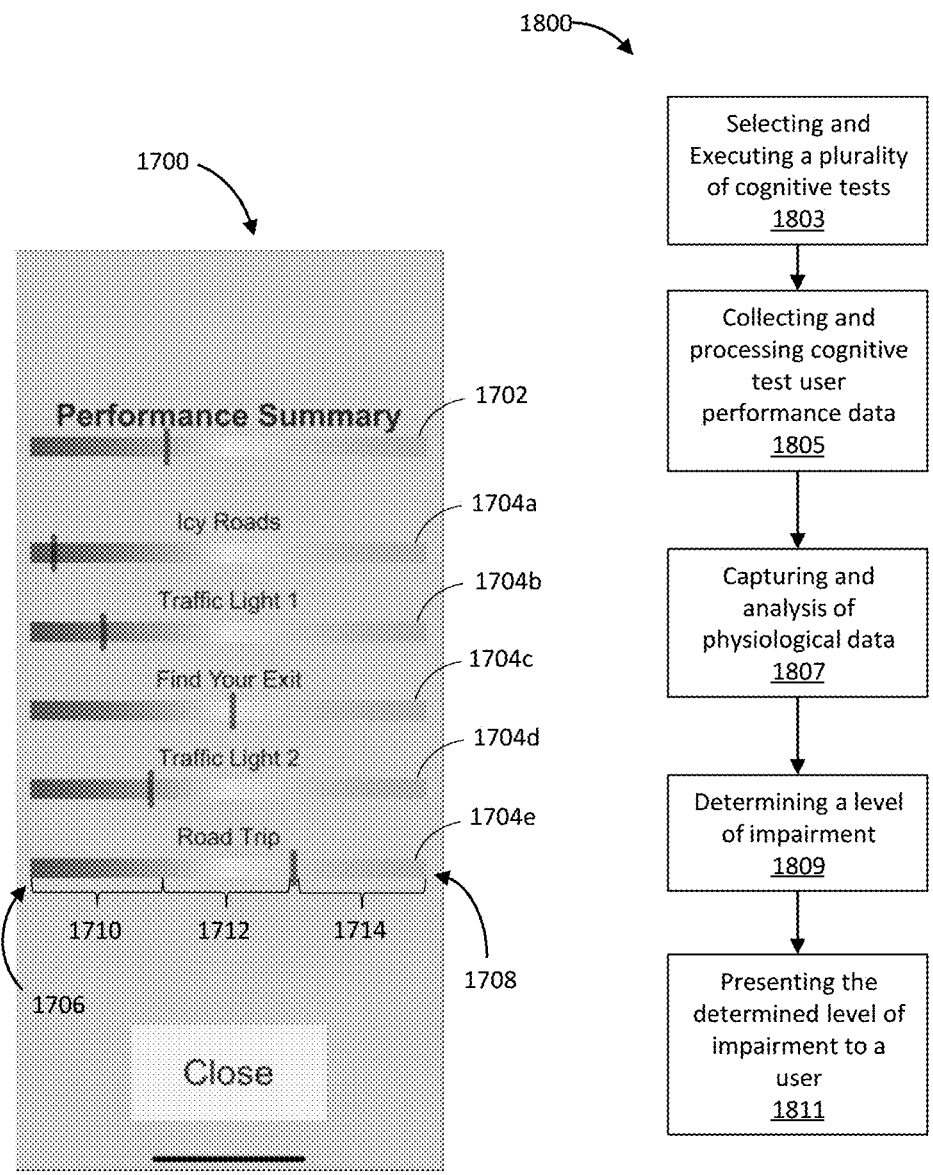
FIG. 17 illustrates one example of a display of results from an impairment assessment analysis performed by an impairment assessment application.
FIG. 18 illustrates an example method of determining a level of impairment of a user with a cognitive impairment assessment application.

FIG. 17 illustrates one example of a display 1700 of results from an impairment assessment analysis performed by an impairment assessment application such as impairment assessment application 104. In the illustrated example, display 1700 includes an overall performance summary 1702 and a display of user performance assessment 1704a-1704e for a plurality of cognitive tests performed by the user. In the illustrated example, each of the performance assessment displays includes a bar on a sliding scale that ranges from more impaired 1706 to less impaired 1708 and may include color coded ranges including a red-colored range 1710 for impairment above a threshold value, a yellow colored range 1712 for a threshold value or range and a green colored range 1714 indicating an impairment below the threshold value. A user or administrator can review overall performance summary 1702 to ascertain a user's overall likely level of impairment relative to a threshold or limit and review the user's performance on each of the cognitive tests from assessments 1704 for a more detailed understanding of which of the user's cognitive domains are the most and least impaired.

Example Methods

FIGS. 18-21 illustrate example methods that may be performed by systems, devices, and software made in accordance with the present disclosure. FIG. 18 illustrates an example method of determining a level of impairment of a user through the use of a cognitive impairment assessment application, such as cognitive impairment assessment application 104, executed on a user device, such as user device 102. In the illustrated example, at block 1803, the method includes selecting and executing a plurality of cognitive tests, such as one or more of cognitive tests 302. Method 1800 may include selecting one or more of any of the plurality of cognitive tests disclosed herein in any combination and in any sequence. In one example the method includes selecting a subset of cognitive tests from a larger battery of tests, the subset of tests specifically designed and configured for determining a level of impairment. In one example, method 1800 includes presenting one or more cognitive tests in a first group of tests and determining a selection and/or sequence of a second group of cognitive tests according to user performance data collected and analyzed from the first group of tests.

In one example a subset of cognitive tests selected and executed specifically for determining a level of impairment include one or more of a first cognitive test in the form of a game that tests psychomotor control 402 including psychomotor compensation and sustained attention 420, for example, cognitive test 500 or 600 or a variation thereof; a second cognitive test in the form of a game that tests a sense of timing 404 by testing the ability to observe and recall a randomly presented timing of an event, response inhibition 410, and sustained attention 420, for example, cognitive test 700 or a variation thereof; a third cognitive test in the form of a game that tests sustained attention 420, divided attention 418, and short term memory 416, for example, cognitive test 800 or 900 or a variation thereof; a fourth cognitive test 302*d* in the form of a game that tests psychomotor control 402 in the form of reaction time, and response inhibition 410, for example, cognitive test 1000 or a variation thereof; and a fifth cognitive test in the form of a game that tests psychomotor control 402 including reaction time and response inhibition 410.

In block 1805, user performance data from the cognitive tests executed at block 1803 are received, stored, and processed by the impairment assessment application. In some examples, user performance data is transmitted from the user device to a cloud-based analysis system, for example, impairment assessment service 124. In some examples, the impairment assessment service may be configured to store user performance data received from the user device in one or more storage systems, such as database 130 and process the user performance data to provide an impairment assessment. Any of a variety of calculation methodologies may be used including calculation of a score or other value relative to a threshold value or range, for example, a threshold value or range representing a limit beyond which a cognitive aptitude may be impaired to an extent that the person may be unable to safely perform a task such as operating a motor vehicle. In some examples, the cloud-based impairment assessment service and/or the impairment assessment application on the user device may be configured to execute a machine learning algorithm configured to compare user performance data to large datasets in a database from prior cognitive tests to determine a selection or sequence of cognitive tests and/or provide an impairment assessment.

In block 1807, the method may include capturing and analysis of physiological data, for example through the execution of physiological testing module 206. Block 1807 may include performing any of the physiological tests described herein, including the capturing and analysis of images of the user's eyes, where the physiological testing occurs separately from the execution of cognitive tests or simultaneously, for example, capturing images of the user's eyes while the user is taking one or more cognitive tests. Physiological data may also include head movements, heart rate, heart rate variability, respiratory rate, and blood pressure which can be collected and processed to determine a likelihood of impairment. In block 1809, method 1800 may include processing the physiological testing data collected at block 1807 and the cognitive test data collected at blocks 1805 and 1807 and determining a level of impairment which may include, in one example, determining whether a user's overall cognitive impairment is above or below a threshold value or range, and in clock 1811, presenting the determined level of impairment to a user, for example, via a GUI displayed on user interface 112.

In other examples, one or more of the illustrated steps of method 1800 may be omitted and/or the sequence of performance of the steps may be varied. For non-limiting example, in some implementations, block 1807 (capturing and processing of physiological information such as images of a user's eyes) may be omitted.

Figures 19, 20:
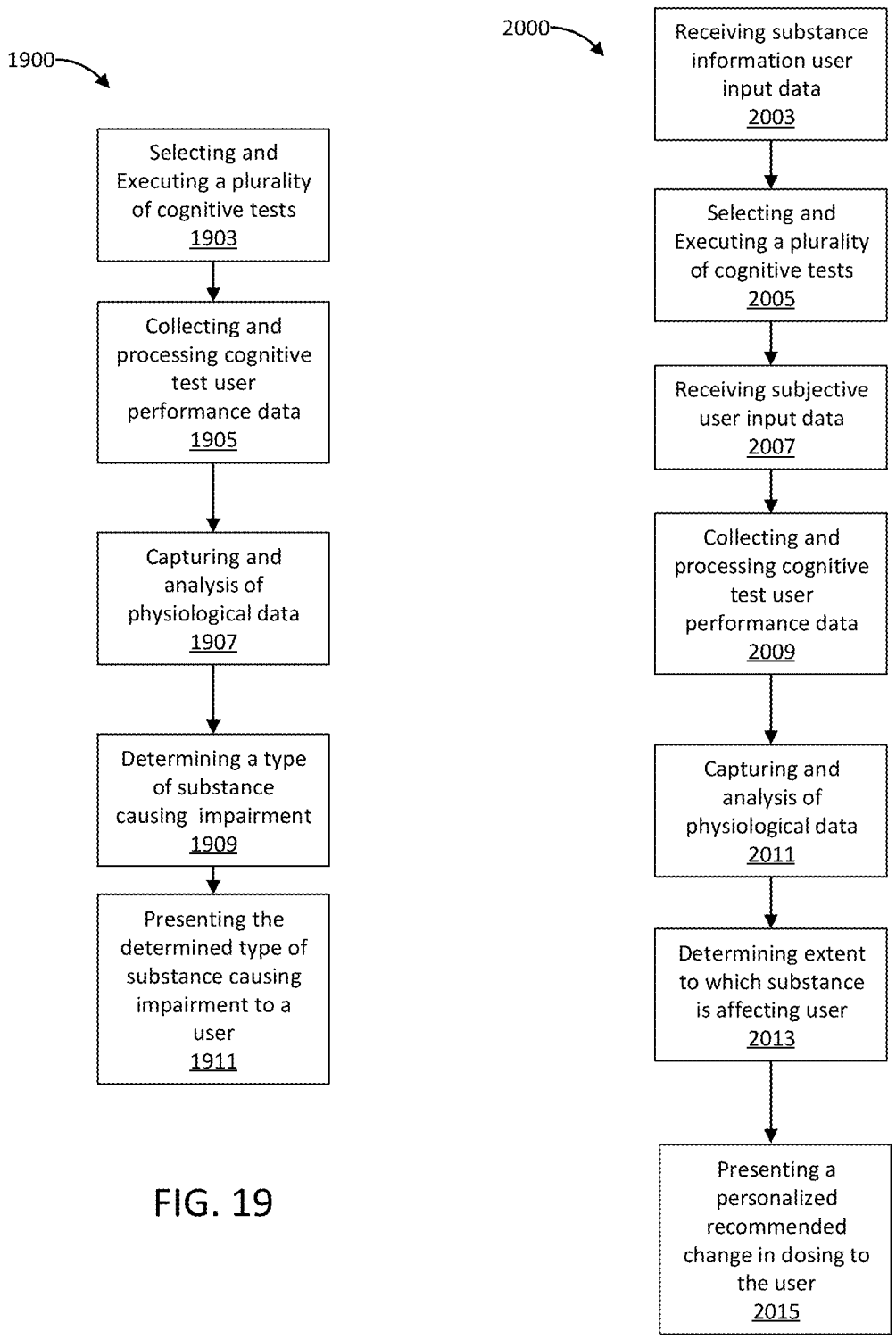
FIG. 19 illustrates an example method of identifying one or more substances that is/are likely causing a cognitive impairment with a cognitive impairment assessment application.
FIG. 20 illustrates an example method of determining a degree to which a substance is affecting a user's cognitive and behavioral abilities and the user's subjective experience while under the influence of the specified substance.

FIG. 19 illustrates an example method of identifying one or more substances that is/are likely causing a cognitive impairment through the use of a cognitive impairment assessment application, such as cognitive impairment assessment application 104, executed on a user device, such as user device 102. In the illustrated example, at block 1903, the method includes selecting and executing a plurality of cognitive tests, such as one or more of cognitive tests 302. Method 1900 may include selecting one or more of any of the plurality of cognitive tests disclosed herein in any combination and in any sequence. In one example the method includes selecting a subset of cognitive tests from a larger battery of tests, the subset of tests specifically designed and configured for determining a type of substance causing an impairment. In one example, method 1900 includes presenting one or more cognitive tests in a first group of tests and determining a selection and/or sequence of a second group of cognitive tests according to user performance data collected and analyzed from the first group of tests.

In one example a subset of cognitive tests selected and executed specifically for determining a substance causing impairment by testing a plurality of cognitive aptitudes that are influenced differently by different kinds of substances. In one example, cognitive tests may include a cognitive test in the form of a game that tests a sense of timing 404 by testing the ability to observe and recall a randomly presented timing of an event, response inhibition 410, and sustained attention 420, for example, cognitive test 700 or a variation thereof; a cognitive test in the form of a game that tests short term memory 416, sustained attention 420, and risk taking, for example, cognitive test 1400 or a variation thereof; and/or a cognitive test in the form of a game that tests creativity 408.

In some examples, a subset of cognitive tests selected and executed specifically for determining a substance causing impairment may be developed utilizing machine learning algorithms and database 130 by, in a first step, collecting training data that includes user performance data from a plurality of cognitive tests, wherein substance information associated with the training data is known, for example from user input in response to questionnaires obtained, for example, with questionnaire module 204 and stored in a database, for example questionnaire data 134. In a second step, executing one or more machine learning algorithms and models to identify patterns in the user performance data that may include particular cognitive tests that are more effective in elucidating a cognitive impairment caused by a first substance or class of substances, such as cannabis, and other cognitive tests more effective at elucidating a cognitive impairment caused by a second substance or class of substances, such as opioids. In some examples, instead of or in addition to identifying separate cognitive tests by substance, the method may include utilizing machine learning algorithms to identify patterns in the training data collected from the performance of a battery of cognitive tests, such as two or more of any of the cognitive tests disclosed herein, to train a machine learning model to determine whether test data collected from the battery of tests indicates a cognitive impairment caused by a particular substance.

At block 1905, the method may include collecting and processing user performance data collected from the tests executed in block 1903 and determining a substance or class of substances that is likely causing an impairment. In some examples, user performance data is transmitted from the user device to a cloud-based analysis system, for example, impairment assessment service 124. In some examples, the impairment assessment service may be configured to store user performance data received from the user device in one or more storage systems, such as database 130 and process the user performance data to provide an impairment assessment. Any of a variety of calculation methodologies may be used including calculation of a score indicating a likelihood of impairment by each of a plurality of substances or classes of substances. For example, impairment assessment application may be configured to display a GUI that includes a list of substances, such as cannabis, alcohol, opioids, etc. and adjacent each listed substance, a determined likelihood of impairment. In one example of method 1900, the impairment assessment application may determine there is a high likelihood, for example, greater than 90% likelihood a user is impaired by a first substance, such as cannabis, and a low likelihood, such as less than a 30% likelihood the user is impaired by a second and third substance, such as alcohol and opioids, and display the results on a user interface such as user interface 112.

In block 1907, the method may include capturing and analysis of physiological data, for example through the execution of physiological testing module 206. Block 1907 may include performing any of the physiological tests described herein, including the capturing and analysis of images of the user's eyes, where the physiological testing occurs separately from the execution of cognitive tests or simultaneously, for example, capturing images of the user's eyes while the user is taking one or more cognitive tests. Physiological data may also include head movements, heart rate, heart rate variability, respiratory rate, and blood pressure which can be collected and processed to determine a likelihood of impairment. In block 1909, method 1900 may include processing the physiological testing data collected at block 1907 and the cognitive test data collected at blocks 1903 and 1905 and determining a likelihood of impairment, and level of impairment, and/or a substance causing the impairment, and in block 1911, presenting the determinations, including likely substance, to a user, for example, via a GUI displayed on user interface 112.

In other examples, one or more of the illustrated steps of method 1900 may be omitted and/or the sequence of performance of the steps may be varied. For non-limiting example, in some implementations, block 1907 (capturing and processing of physiological information such as images of a user's eyes) may be omitted.

FIG. 20 illustrates an example method 2000 of determining a degree to which a substance is affecting a user's cognitive and behavioral abilities and the user's subjective experience while under the influence of the specified substance. Method 2000 may be performance with a cognitive impairment assessment application, such as cognitive impairment assessment application 104, executed on a user device, such as user device 102. In the illustrated example, at block 2003, method 2000 includes receiving substance information and user input data. For example, a user may be prompted to enter one or more of substance class, substance type, dosage, potency, timing, and context of use. In block 2005, the method includes selecting and executing a plurality of cognitive tests, such as one or more of cognitive tests 302. Method 2000 may include selecting one or more of any of the plurality of cognitive tests disclosed herein in any combination and in any sequence. In one example the method includes adapting a sequence according to a user's preference and performance on one or more initial cognitive tests.

In block 2007, subjective user input data, such as data relating to a user's mood, emotions, and behavioral experience is received before, after, or concurrently with block 2005, for example by prompting the user to enter the subjective information via user interface 112. At block 2009 user performance data from the cognitive tests executed at block 2005 are received, stored, and processed by the impairment assessment application. In some examples, user performance data is transmitted from the user device to a cloud-based analysis system, for example, impairment assessment service 124 and analyzed using any of the methodologies disclosed herein.

In block 2011, the method may include capturing and analysis of physiological data, for example through the execution of physiological testing module 206. Block 2011 may include performing any of the physiological tests described herein, including the capturing and analysis of images of the user's eyes, where the physiological testing occurs separately from the execution of cognitive tests or simultaneously, for example, capturing images of the user's eyes while the user is taking one or more cognitive tests. Physiological data may also include head movements, heart rate, heart rate variability, respiratory rate, and blood pressure which can be collected and processed to determine a likelihood of impairment. In block 2013, the method may include further processing of objective, subjective and physiological data to determine an extent to which the substance is affecting the user and in block 2015, the method may include presenting a personalized recommendation for a change of dosing or an alternate substance to the user. For example, in block 2007, a user may have specified an affect he or she is desiring from the substance, such as an affect on behavior, mood, concentration, energy level, etc. The method may include recommending a decrease, increase, or no change in dosage, or an alternate type of substance, for example, a different type of substance for achieving the user's desired result.

In other examples, one or more of the illustrated steps of method 2000 may be omitted and/or the sequence of performance of the steps may be varied. For non-limiting example, in some implementations, block 2011 (capturing and processing of physiological information such as images of a user's eyes) may be omitted.

Figure 21:
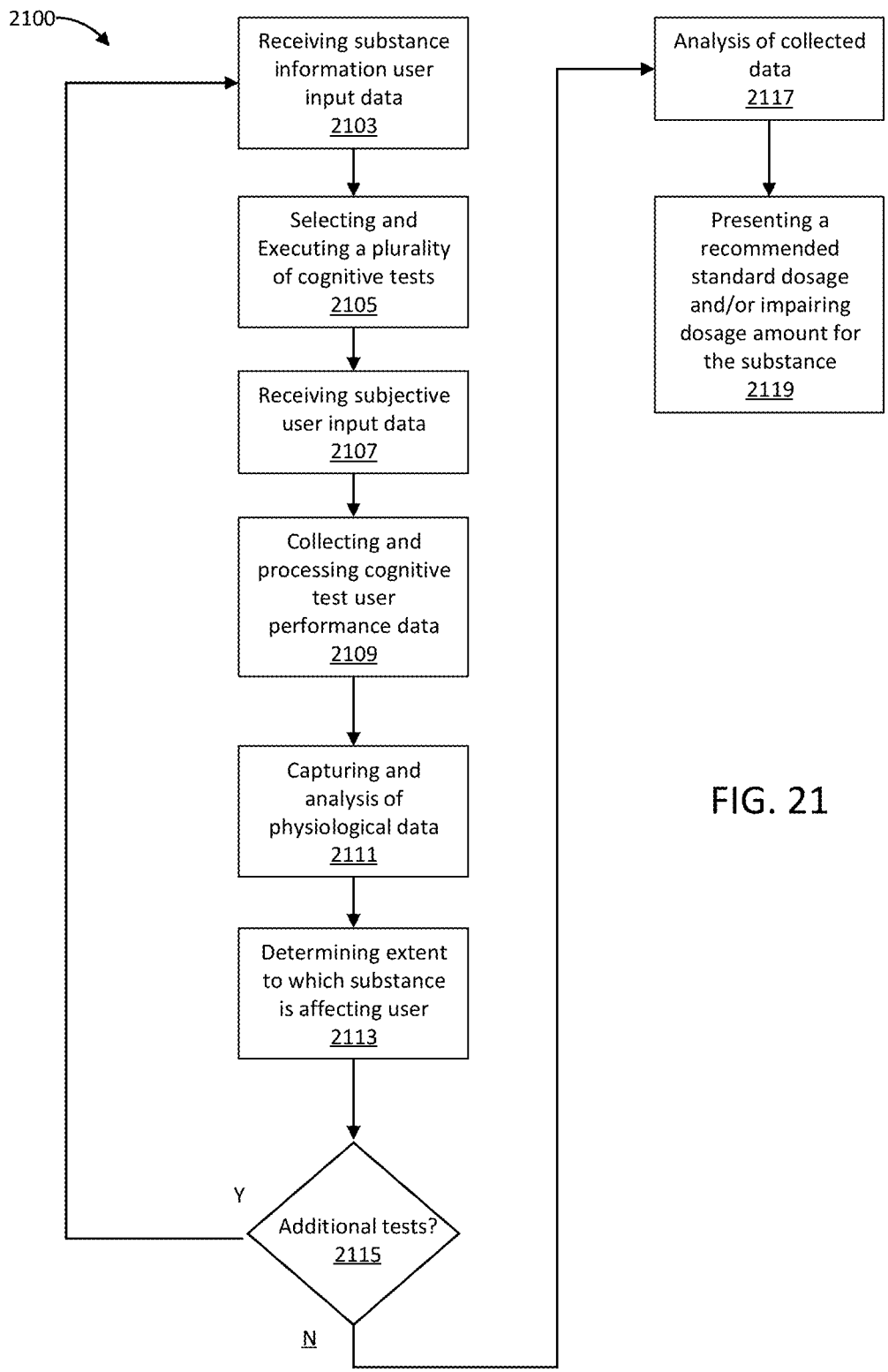
FIG. 21 illustrates an example method of determining a quantity and characteristics of a standard impairing and/or desirable dose threshold for a substance.

FIG. 21 illustrates an example method 2100 of determining a quantity and characteristics of a standard impairing and/or desirable dose threshold for a substance. Method 2100 may be performance with a cognitive impairment assessment application, such as cognitive impairment assessment application 104, executed on a user device, such as user device 102. In the illustrated example, at block 2103, method 2100 includes receiving substance information and user input data. For example, a user may be prompted to enter one or more of substance class, substance type, dosage, potency, timing, and context of use. In block 2105, the method includes selecting and executing a plurality of cognitive tests, such as one or more of cognitive tests 302. Method 2100 may include selecting one or more of any of the plurality of cognitive tests disclosed herein in any combination and in any sequence. In one example the method includes adapting a sequence according to a user's preference and performance on one or more initial cognitive tests.

In block 2107, subjective user input data, such as data relating to a user's mood, emotions, and behavioral experience is received before, after, or concurrently with block 2105, for example by prompting the user to enter the subjective information via user interface 112. At block 2109 user performance data from the cognitive tests executed at block 2105 are received, stored, and processed by the impairment assessment application. In some examples, user performance data is transmitted from the user device to a cloud-based analysis system, for example, impairment assessment service 124 and analyzed using any of the methodologies disclosed herein.

In block 2111, the method may include capturing and analysis of physiological data, for example through the execution of physiological testing module 206. Block 2111 may include performing any of the physiological tests described herein, including the capturing and analysis of images of the user's eyes, where the physiological testing occurs separately from the execution of cognitive tests or simultaneously, for example, capturing images of the user's eyes while the user is taking one or more cognitive tests. Physiological data may also include head movements, heart rate, heart rate variability, respiratory rate, and blood pressure which can be collected and processed to determine a likelihood of impairment. In block 2113, the method may inclue further processing of objective, subjective and physiological data to determine an extent to which the substance is affecting the user. In block 2115 the method includes determining whether additional users are available to test and if yes blocks 2103-2113 are performed for additional users and if no, at block 2117 the method includes further analysis of the objective, subjective, and physiological data collected from a plurality of users that have each taken the same substance, in some examples, in varying amounts to determine a recommended dosing for normal use and/or to determine an impairing dosage threshold beyond which it is, for example, unsafe to operate a motor vehicle. Block 2117 may include analysis of large data sets of objective and subjective information to identify a dosage of a substance beyond which, undesirable effects such as drowsiness, adverse impact to one or more cognitive aptitudes, and/or adverse impact on mood or behavior. In block 2119 the method may include presenting the recommended dosing for normal use and/or the impairing dosage threshold, for example on a display of user interface 112.

In other examples, one or more of the illustrated steps of method 2100 may be omitted and/or the sequence of performance of the steps may be varied. For non-limiting example, in some implementations, block 2111 (capturing and processing of physiological information such as images of a user's eyes) may be omitted.

Any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 22:
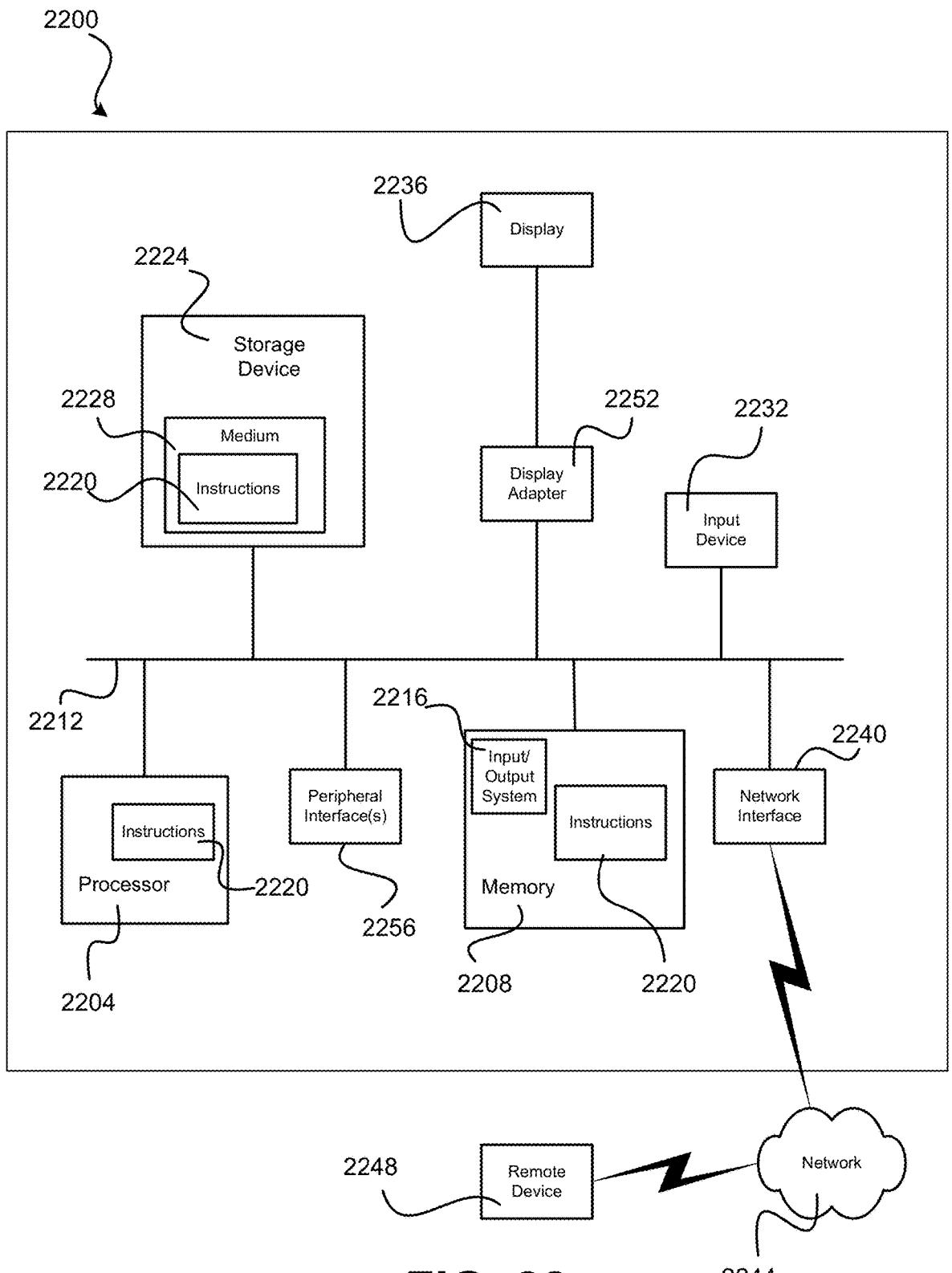
FIG. 22 is a functional block diagram of an example computing system.

FIG. 22 shows a diagrammatic representation of one embodiment of a computing device in the exemplary form of a computer system 2200 within which a set of instructions for causing a system, such as the impairment assessment system of FIG. 1, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 2200 includes a processor 2204 and a memory 2208 that communicate with each other, and with other components, via a bus 2212. Bus 2212 may include any of several types of bus structures including, but not limited to, a memory bus, a memory controller, a peripheral bus, a local bus, and any combinations thereof, using any of a variety of bus architectures.

Memory 2208 may include various components (e.g., machine-readable media) including, but not limited to, a random access memory component, a read only component, and any combinations thereof. In one example, a basic input/output system 2216 (BIOS), including basic routines that help to transfer information between elements within computer system 2200, such as during start-up, may be stored in memory 2208. Memory 2208 may also include (e.g., stored on one or more machine-readable media) instructions (e.g., software) 2220 embodying any one or more of the aspects and/or methodologies of the present disclosure. In another example, memory 2208 may further include any number of program modules including, but not limited to, an operating system, one or more application programs, other program modules, program data, and any combinations thereof.

Computer system 2200 may also include a storage device 2224. Examples of a storage device (e.g., storage device 2224) include, but are not limited to, a hard disk drive, a magnetic disk drive, an optical disc drive in combination with an optical medium, a solid-state memory device, and any combinations thereof. Storage device 2224 may be connected to bus 2212 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 2224 (or one or more components thereof) may be removably interfaced with computer system 2200 (e.g., via an external port connector (not shown)). Particularly, storage device 2224 and an associated machine-readable medium 2228 may provide nonvolatile and/or volatile storage of machine-readable instructions, data structures, program modules, and/or other data for computer system 2200. In one example, software 2220 may reside, completely or partially, within machine-readable medium 2228. In another example, software 2220 may reside, completely or partially, within processor 2204.

Computer system 2200 may also include an input device 2232. In one example, a user of computer system 2200 may enter commands and/or other information into computer system 2200 via input device 2232. Examples of an input device 2232 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 2232 may be interfaced to bus 2212 via any of a variety of interfaces (not shown) including, but not limited to, a serial interface, a parallel interface, a game port, a USB interface, a FIRE-WIRE interface, a direct interface to bus 2212, and any combinations thereof. Input device 2232 may include a touch screen interface that may be a part of or separate from display 2236, discussed further below. Input device 2232 may be utilized as a user selection device for selecting one or more graphical representations in a graphical interface as described above.

A user may also input commands and/or other information to computer system 2200 via storage device 2224 (e.g., a removable disk drive, a flash drive, etc.) and/or network interface device 2240. A network interface device, such as network interface device 2240, may be utilized for connecting computer system 2200 to one or more of a variety of networks, such as network 2244, and one or more remote devices 2248 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 2244, may employ a wired and/or a wireless mode of communication. In general, any network topology may be used. Information (e.g., data, software 2220, etc.) may be communicated to and/or from computer system 2200 via network interface device 2240.

Computer system 2200 may further include a video display adapter 2252 for communicating a displayable image to a display device, such as display device 2236. Examples of a display device include, but are not limited to, a liquid crystal display (LCD), a cathode ray tube (CRT), a plasma display, a light emitting diode (LED) display, and any combinations thereof. Display adapter 2252 and display device 2236 may be utilized in combination with processor 2204 to provide graphical representations of aspects of the present disclosure. In addition to a display device, computer system 2200 may include one or more other peripheral output devices including, but not limited to, an audio speaker, a printer, and any combinations thereof. Such peripheral output devices may be connected to bus 2212 via a peripheral interface 2256. Examples of a peripheral interface include, but are not limited to, a serial port, a USB connection, a FIREWIRE connection, a parallel connection, and any combinations thereof.

The present disclosure also includes a non-transitory machine-readable storage medium containing machine-readable instructions configured to cause a processor to perform operations comprising any of the methods disclosed herein, including any of the methods recited in claims 1-25 of the original application.

For example, a non-transitory machine-readable storage medium containing machine-readable instructions configured to cause a processor to perform operations comprising: selecting and executing, by a processor, a plurality of cognitive tests, each of the cognitive tests in the form of a video game displayed on a user interface of the computing device, wherein the video games include at least one of: a first video game configured to test psychomotor compensation and including instructions for execution by a processor for displaying a user control element and an object on the user interface, the object configured to move in a periodic or random manner, the user control element for controlling a position of the object in response to the periodic or random movements of the object; a second video game configured to test a user's sense of timing and including instructions for execution by a processor for displaying at least one time-varying stimuli, the second video game configured to test a user's ability to recall and predict a time duration of the time varying stimuli; and a third video game configured to test a user's sustained attention and divided attention and including instructions for execution by a processor for displaying sequences of symbols for the user to remember and recognize; processing, by the processor, user performance data from the user's performance of the cognitive tests; and determining, by the processor, an impairment assessment from the user performance data.

In another example, a non-transitory machine-readable storage medium containing machine-readable instructions configured to cause a processor to perform operations comprising: executing a first video game on the user device, the executing the first video game including:

- displaying on a user interface of the user device, a user control element and an object;
- moving the object in a plurality of directions on the user interface;
- receiving user controls via the user control element to control a position of the object;
- collecting user performance data on the user's ability to control the position of the object;
- calculating a user performance variable for psychomotor control according to the user performance data from the first video game;
- executing a second video game on the user device, the executing the second video game including:
- displaying at least one example time-varying stimuli on the user interface of the user device;
- receiving user control signals via the user interface representing when the user predicts the time-varying stimuli will be displayed according to the example time-varying stimuli;
- collecting user performance data on the user's ability to predict when the time-varying stimuli would be displayed;

calculating a user performance variable for a sense of timing according to the user performance data from the second video game; and executing a third video game on the user device, the executing the third video game including:

displaying a time-varying sequence of symbols that include a target sequence;

receiving user control signals via the user interface representing when the user observes the target sequence;

collecting user performance data on the user's ability to observe when the target sequence is displayed;

calculating a user performance variable for sustained attention and short term memory a according to the user performance data from the third video game.

In another example, a non-transitory machine-readable storage medium containing machine-readable instructions configured to cause a processor to perform operations comprising: presenting a first one of the plurality of video games on the user device;

receiving, at the impairment assessment service, user performance data from the user's performance on the first video game;

selecting, by the impairment assessment service, a second one of the plurality of video games according to the user performance data from the user's performance on the first video game;

presenting the second one of the plurality of video games on the user device;

receiving, at the impairment assessment service, user performance data from the user's performance on the second video game;

determining an impairment assessment according to the user performance data from the user's performance on the first and second video games.

The present disclosure also includes computer devices and systems designed to perform operations comprising any of the methods disclosed herein, including any of the methods recited in claims 1-25 of the original application, including a user device configured to execute an impairment assessment application and that is communicatively coupled to a cloud-based impairment assessment service.

The foregoing has been a detailed description of illustrative embodiments of the disclosure. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this disclosure. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present disclosure. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this disclosure.

What is claimed is:

1. A method of performing an impairment assessment with an impairment assessment application executed on a computing device, the method comprising:

executing, by a processor, a sense of timing video game configured to test a user's sense of timing and including instructions for:

instructing the user to select a user control element when the user determines a redetermined time duration has elapsed;

receiving the user selection of the user control element; and determining, by the processor, the impairment assessment according to a plurality of the user selections, wherein the determining includes identifying a first class or type of substance in response to the user selections being inaccurate and including overpredictions of the predetermined time duration and identifying a second class or type of substance in response to the user selections being inaccurate and underpredicting the predetermined time duration.

2. The method of claim 1, wherein the determining the impairment assessment includes calculating, by the processor, a performance metric according to the plurality of user selections and comparing the calculated performance metric to a threshold value.

3. The method of claim 1, wherein the determining the impairment assessment includes executing, by the processor, a machine learning algorithm that compares user performance data from the sense of timing video game to training data to determine a likelihood of impairment.

4. The method of claim 1, further comprising:

executing, by the processor, a first video game in response to the user selections being inaccurate and including overpredictions of the predetermined time duration; and executing, by the processor, a second video game in response to the user selections being inaccurate and underpredicting the predetermined time duration.

5. The method of claim 4, wherein the second video game is configured to test response inhibition.

6. The method of claim 5, wherein the second video game includes instructions for execution by the processor for displaying a plurality of user control elements on a user interface of the computing device and testing a user's ability to rapidly select the control elements and then stop when a stop signal is displayed and/or emitted by the computing device.

7. The method of claim 1, further comprising receiving physiological data, wherein the physiological data includes images of at least a portion of a user's face captured with an image capture device coupled to the computing device, the images captured concurrently with the execution of the sense of timing video game, wherein the determining the impairment assessment includes determining the impairment assessment from the user performance data and the physiological data.

8. The method of claim 7, further comprising varying a brightness of a display of the user interface and/or controlling a brightness of a light source operably coupled to the computing device to increase or decrease a brightness of emitted light during the execution of the sense of timing video game to evoke a pupillary response in the user, the physiological data including images of pupil dilation.

9. The method of claim 7, wherein the physiological data includes images of a user's eyes captured during performance of the sense of timing video game, the determining the impairment assessment including analysis, by the processor, of the images with a machine vision algorithm to detect the presence of saccadic movement and/or eye convergence.

10. The method of claim 1, wherein the determining the impairment assessment includes determining a user's level of cognitive impairment and determining whether the cognitive impairment is above or below a threshold value or range.

11. The method of claim 10, further comprising selecting and executing a plurality of video games that test a plurality of cognitive aptitudes required for the safe operation of a motor vehicle, the cognitive aptitudes including psychomotor control, sustained attention, divided attention, and response inhibition.

12. The method of claim 11, wherein the selecting and executing a plurality of video games includes adapting a sequence of presentation of the plurality of video games according to the user's performance on an initial one of the video games.

13. A method of performing a physiological neurocognitive and/or behavioral assessment with an impairment assessment system, the system including a cloud-based impairment assessment service and a user device, the method including:
   executing a first video game on the user device, the executing the first video game including:
      displaying on a user interface of the user device, a user control element and an object;
      moving the object in a plurality of directions on the user interface;
      receiving user controls via the user control element to control a position of the object in response to the moving of the object;
      collecting user performance data on the user's ability to control the position of the object;
      calculating a user performance variable for psychomotor control according to the user performance data from the first video game;
   executing a second video game on the user device, the executing the second video game including:
      displaying at least one example time-varying stimuli on the user interface of the user device;
      receiving user control signals via the user interface representing when the user predicts the time-varying stimuli will be displayed according to the example time-varying stimuli;
      collecting user performance data on the user's ability to predict when the time-varying stimuli would be displayed;
      calculating a user performance variable for a sense of timing according to the user performance data from the second video game; and
   executing a third video game on the user device, the executing the third video game including:
      displaying a time-varying sequence of symbols that include a target sequence;
      receiving user control signals via the user interface representing when the user observes the target sequence;
      collecting user performance data on the user's ability to observe when the target sequence is displayed;
      calculating a user performance variable for sustained attention and short term memory according to the user performance data from the third video game;
   wherein the method further includes executing at least one of the first and third video games in response to determining the user performance data from the second video game indicates the user predictions are inaccurate and includes overpredictions of the time durations; and
   executing, by a processor, a fourth video game in response to determining the user predictions from the second video game are inaccurate and underpredict the time duration.

14. The method of claim 13, wherein the executing the third video game further includes:
   displaying an intermittent divided attention stimuli concurrently with the displaying the time-varying sequence; and
   receiving user control signals via the user interface representing when the user observes the divided attention stimuli;
   wherein the collecting user performance data further includes collecting user performance data on the user's ability to observe when the divided attention stimuli are displayed.

15. The method of claim 13, further comprising determining a type of substance that is likely causing a cognitive impairment according to the user performance data from the second video game.

16. The method of claim 13, further comprising:
   receiving user input data specifying substance information including substance class or type, dosage information, and user subjective experience information specifying the subjective impact the substance is having on the user;
   comparing the calculated user performance variables and subjective experience information to user performance variables and subjective experience information from other users with the same substance type and the same and alternate dosages;
   determining a recommended change in dosing according to the comparing step.

17. The method of claim 1, wherein the sense of timing video game further includes instructions for executing at least one round of the sense of timing video game, the at least one round including an observation portion that includes displaying a visual stimuli after the predetermined time duration has elapsed and a subsequent testing portion including instructing the user to predict, based on the observation portion, when the visual stimuli will appear, the method including receiving the user selection of the user control element when the user determines the predetermined time duration has elapsed.

18. The method of claim 17, wherein the executing at least one round includes executing a plurality of rounds of the sense of timing video game, wherein the predetermined time duration is varied between at least some of the plurality of rounds.

19. The method of claim 4, wherein the first video game is configured to test at least one of psychomotor compensation, sustained attention, divided attention, and short term memory.

20. The method of claim 19, wherein the first video game is a psychomotor compensation video game and includes instructions for:

displaying a second user control element, an object, and boundaries on the user interface, the object configured to move in a periodic or random manner, the second user control element for controlling a position of the object in response to the periodic or random movement of the object to maintain the object within the boundaries;

receiving user selections of the second user control element; and determining, according to the user selections, whether the second user control element was operated in a direction different from a correct direction for maintaining the object within the boundaries.

21. The method of claim 1, wherein the first type or class of substance is a stimulant and the second type or class of substance is cannabis.

22. The method of claim 1, further comprising, executing, by the processor, a video game designed to test risk taking in response to the user selections being accurate and identifying a third class or type of substance in response to the risk taking video game indicating enhanced risk taking.

23. The method of claim 22, wherein the third class or type of substance includes at least one of alcohol and a benzodiazepine.

24. A method of performing an impairment assessment with an impairment assessment application executed on a computing device, the method comprising:

executing, by a processor, a plurality of video games including a sense of timing video game and a psychomotor compensation video game; and identifying, by the processor, a type or class of substance according to user performance data from the execution of the plurality of video games, wherein the identifying includes:

identifying a stimulant in response to the user performance data from the sense of timing video game underpredicting a target time duration; and identifying cannabis in response to the user performance data from the sense of timing video game overpredicting the target time duration and the user performance data from the psychomotor compensation video game indicating an impairment.

25. The method of claim 24, further comprising:

executing, by the processor, a sustained attention and divided attention video game; and wherein the identifying further includes identifying a stimulant in response to the user performance data from the sustained attention and divided attention video game not indicating an impairment and identifying cannabis or alcohol in response to the sustained attention and divided attention video game indicating an impairment.

26. The method of claim 24, further comprising identifying alcohol in response to the sustained attention and divided attention or psychomotor compensation video game indicating an impairment and the user performance data from the sense of timing video game accurately predicting the target time duration.

27. The method of claim 24, further comprising:

executing, by the processor, a risk taking video game; and wherein the identifying further includes identifying the cannabis in response to the user performance data from the risk taking video game not indicating enhanced risk taking and includes identifying alcohol or a benzodiazepine in response to the risk taking video game indicating enhanced risk taking.

\* \* \* \* \*